United States Patent
Naslund et al.

(10) Patent No.: US 9,675,718 B2
(45) Date of Patent: Jun. 13, 2017

(54) DEVICE AND METHOD FOR IRRADIATING OBJECTS WITH ELECTRON BEAM

(71) Applicant: Tetra Laval Holdings & Finance S.A., Pully (CH)

(72) Inventors: Lars-Ake Naslund, Furulund (SE); Kristoffer Bengtsson, Lund (SE); Hakan Mellbin, Horby (SE); Hans Hallstadius, Lund (SE); Fredrik Hansen, Bjarred (SE); Marco Lavalle, Formigine (IT)

(73) Assignee: TETRA LAVAL HOLDINGS & FINANCE S.A., Pully (CH)

( * ) Notice: Subject to any disclaimer, the term of this patent is extended or adjusted under 35 U.S.C. 154(b) by 65 days.

(21) Appl. No.: 14/649,242

(22) PCT Filed: Nov. 29, 2013

(86) PCT No.: PCT/EP2013/075082
§ 371 (c)(1),
(2) Date: Jun. 3, 2015

(87) PCT Pub. No.: WO2014/086674
PCT Pub. Date: Jun. 12, 2014

(65) Prior Publication Data
US 2015/0306261 A1    Oct. 29, 2015

(30) Foreign Application Priority Data
Dec. 3, 2012    (EP) .................................... 12195285

(51) Int. Cl.
*A61N 5/00*    (2006.01)
*G01J 1/42*    (2006.01)
(Continued)

(52) U.S. Cl.
CPC .............. *A61L 2/087* (2013.01); *B65B 55/08* (2013.01); *G01T 1/02* (2013.01); *H01J 33/00* (2013.01);
(Continued)

(58) Field of Classification Search
CPC ............................... A61L 2/00; B67C 7/0073
(Continued)

(56) References Cited

U.S. PATENT DOCUMENTS

| 4,608,493 A | 8/1986 | Hayafuji |
| 2007/0090303 A1* | 4/2007 | Kristiansson ...... G01R 19/0061 250/492.3 |

(Continued)

FOREIGN PATENT DOCUMENTS

WO    WO 2007/050007 A1    5/2007

OTHER PUBLICATIONS

International Search Report (PCT/ISA/210) mailed on Jun. 17, 2014, by the European Patent Office as the International Searching Authority for International Application No. PCT/EP2013/075082.

*Primary Examiner* — Monzer R Chorbaji
(74) *Attorney, Agent, or Firm* — Buchanan Ingersoll & Rooney PC

(57) ABSTRACT

The present invention relates to an irradiation device for irradiating objects with electron beams. The irradiation device comprises at least one electron beam emitter having an electron exit window and at least one sensor device for detecting a first dose control parameter of the electron beam. The electron beam emitter is adapted to move past the sensor device such that the electron beam emitted from the electron exit window passes within a sensing area of the sensor device. The sensor device comprises more than one conductor each having a conductor surface in the sensing area of the sensor device, and the conductor surface is adapted to be (Continued)

exposed to electrons of the electron beam. The invention also relates to a method.

15 Claims, 12 Drawing Sheets

(51) Int. Cl.
*A61L 2/00* (2006.01)
*B01J 19/08* (2006.01)
*A61L 2/08* (2006.01)
*B65B 55/08* (2006.01)
*H01J 33/00* (2006.01)
*G01T 1/02* (2006.01)

(52) U.S. Cl.
CPC ....... *A61L 2202/14* (2013.01); *A61L 2202/23* (2013.01)

(58) Field of Classification Search
USPC ....... 422/1, 3, 22, 119, 186; 250/492.3, 395, 250/397
See application file for complete search history.

(56) References Cited

U.S. PATENT DOCUMENTS

| | | |
|---|---|---|
| 2007/0114432 A1 | 5/2007 | Kristiansson et al. |
| 2011/0012030 A1 | 1/2011 | Bufano et al. |
| 2011/0012032 A1* | 1/2011 | Bufano .................. A61L 2/087 |
| | | 250/492.3 |

* cited by examiner

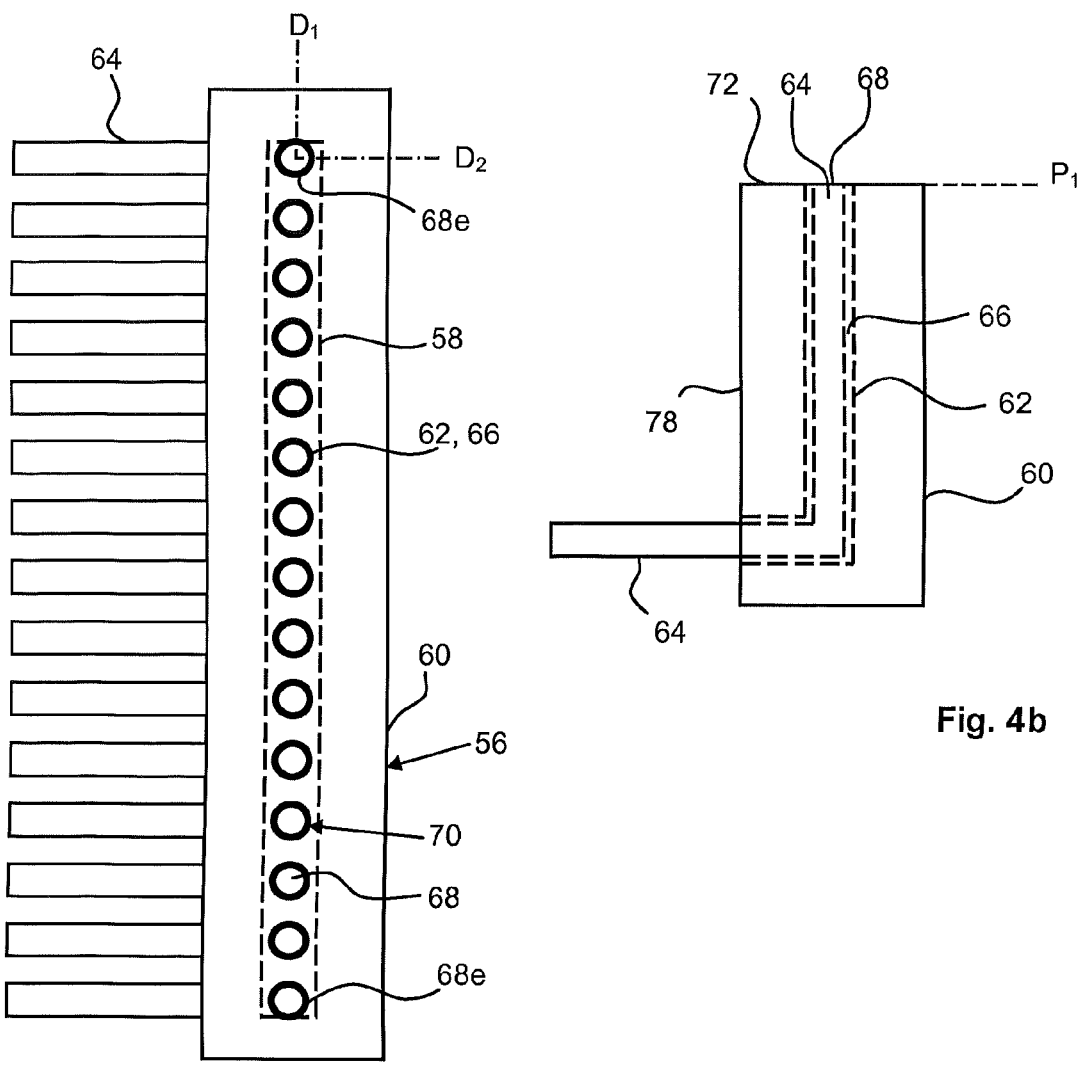
Fig. 4a
Fig. 4b
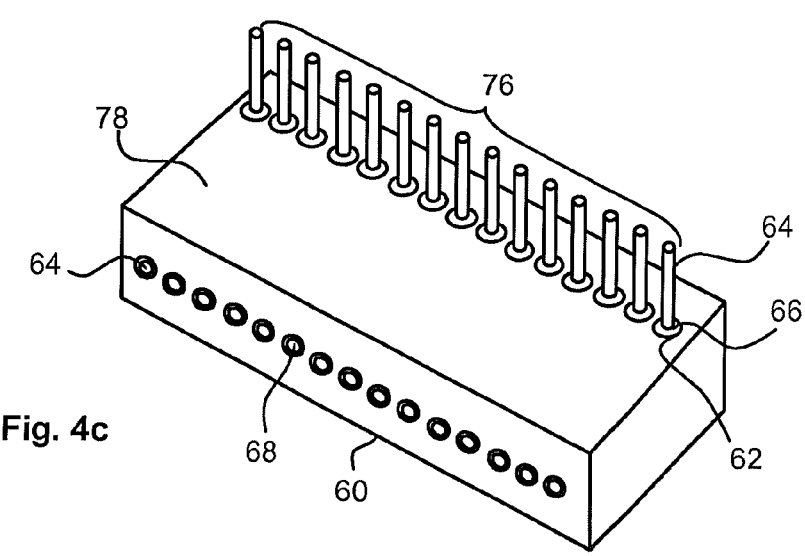
Fig. 4c

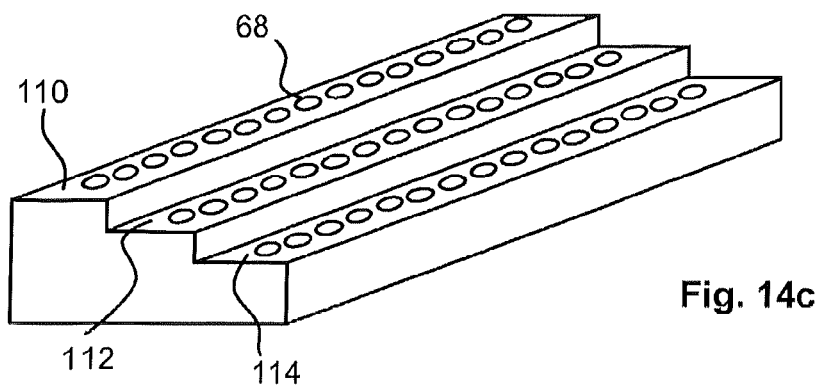
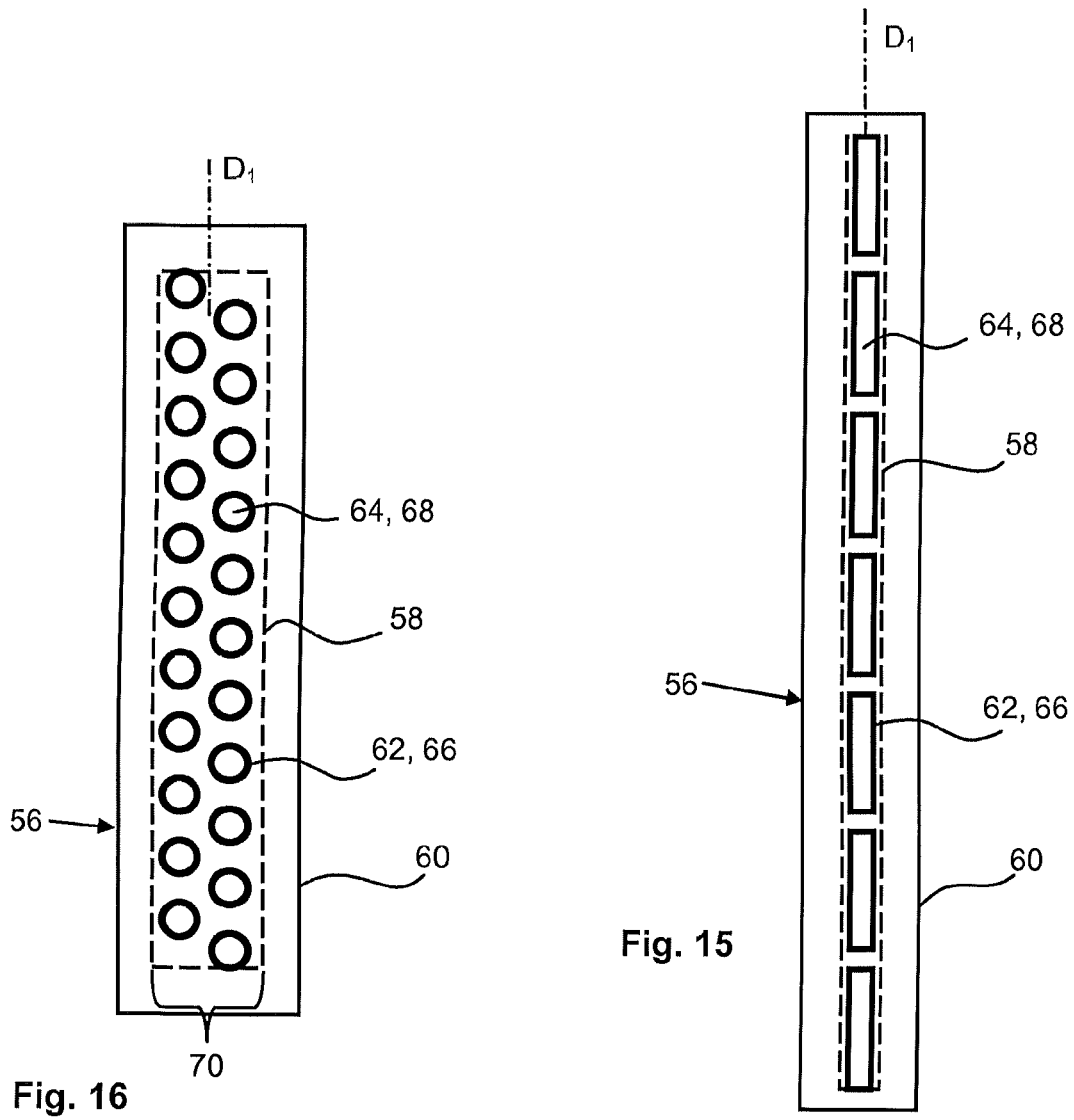
Fig. 14c
Fig. 15
Fig. 16

DEVICE AND METHOD FOR IRRADIATING OBJECTS WITH ELECTRON BEAM

FIELD OF THE INVENTION

The present invention relates to a device and method for irradiating objects with electron beams.

BACKGROUND OF THE INVENTION

Within the food industry, it is common practice to pack liquid and partly liquid food products in packaging containers manufactured from a packaging laminate comprising a core layer of paper or paperboard and one or more barrier layers of, for example, polymer material or aluminium foil.

An increasingly common packaging type is the "carton bottle" manufactured in a filling machine in that packaging blanks of the above-described packaging laminate are formed and sealed as a sleeve. Said sleeve is closed in one end in that a top of thermoplastic material is injection moulded directly on the sleeve end portion. The sheets of packaging laminate may be cut from a magazine reel of packaging laminate.

When the top is finished the packaging container is ready to be filled with product through the still open bottom, and then sealed and finally folded. Before the filling operation the packaging container undergoes treatment. If distribution and storage is to be made in chilled temperature the packaging container is disinfected, whereas if distribution and storage is to be made in ambient temperature, the packaging container needs to be sterilized. A conventional way of sterilizing a ready-to-fill packaging container is to use hydrogen peroxide, preferably in gas phase.

Another way to sterilize such packaging containers is to irradiate it by means of a low voltage electron beam emitted from an electron beam emitter. An example of linear irradiation by electron beam of ready-to-fill packaging containers is disclosed in the international patent publication WO 2005/002973. The electron beam emitter is cylindrical with an electron exit window positioned at one of the distal ends. The packaging container is lifted to surround the electron beam emitter during the sterilization cycle. Other examples of irradiation of packaging containers, in these cases PET bottles, are described in for example WO 2011/011079 and EP 2 371 397, the latter describing a rotary system. In these systems emitters are used having a diameter small enough to be passed through a neck portion of the bottles.

In order to monitor correct operation of the electron beam emitters, and thereby being able to secure sterility assurance level, it is common practise to perform dosimetry tests. These tests are made regularly, generally daily, throughout the lifetime of the electron beam emitter. In general, dosimetry tests involve adding a dosimeter means, i.e. a patch reacting on radiation exposure, to a packaging container to measure if a correct absorbed dose is obtained during radiation. At the same time measurements of voltage and current are made in the electron beam emitter. The current over the filament is measured by comparing the current fed to the filament and current leaving the filament. In this way it is possible to determine the amount of electrons emitted from the filament. In addition, the voltage, i.e. the electric potential, between the electron exit window and the filament is measured. The measured value of voltage and current is then used as a set value during production of packaging containers. The current and voltage are continuously monitored during production, and as long as the value is not lower than the set value it is assumed that the packaging containers receive the correct dose.

SUMMARY OF THE INVENTION

An object of the invention is to provide an irradiation device in which on-line measurement and control of the functionality of the electron beam emitter is improved. Said object is achieved by providing an irradiation device for irradiating objects with electron beams. Said irradiation device comprises at least one electron beam emitter having an electron exit window, and at least one sensor device for detecting a first dose control parameter of the electron beam. Said electron beam emitter is adapted to move past the sensor device such that the electron beam emitted from the electron exit window passes within a sensing area of the sensor device, and said sensor device comprises more than one conductor each having a conductor surface in the sensing area of the sensor device, which conductor surface is adapted to be exposed to electrons of said electron beam.

In one or more embodiments the first dose control parameter is electrical current and wherein the sensor device is connected to a current signal module adapted to measure any electrical current from each of said conductors.

In one or more embodiments the current signal module is in communication with a dose processing module.

In one or more embodiments the dose processing module is adapted to collect first dose control parameter measurements made at different times, during the passage of the electron beam over the sensor device, to generate an image of the electron beam.

In one or more embodiments the conductors of the sensor device are arranged along a line being directed substantially perpendicular to a direction of the movement of the electron beam emitter over the sensor device.

In one or more embodiments the sensing area of the sensor device at least covers the extension of the entire electron beam in a plane of the sensing area and wherein the first control parameter is detected once during the passage of the electron beam over the sensor device.

In one or more embodiments the first dose control parameter is processed, in the dose processing module, together with second dose control parameters to create dose information comprising dose rate (kGy/s) per area unit of the electron beam delivered from the electron beam emitter in the sensing area.

In one or more embodiments the second dose control parameters comprise current and voltage fed to the electron beam emitter and position of the electron beam emitter in relation to each conductor of the sensor device.

In one or more embodiments the dose processing module is in communication with an emitter control module and an irradiation control module. The second dose control parameters are adapted to be sent to the dose processing module from said emitter control module and said irradiation control module.

In one or more embodiments the emitter control module is connected to means for measuring the current over a filament of the electron beam emitter and the voltage between the electron exit window and said filament.

In one or more embodiments the dose processing module is adapted to provide a feedback signal to the irradiation device control module if the dose rate in one or several of the area units is not within an acceptable, pre-set dose rate range.

In one or more embodiments said sensor device comprises a support in which the conductors are arranged. Said conductors are electrically insulated from said support.

In one or more embodiments the dose processing module is able to generate a 2D image or 2D matrix based on the dose rate per area unit of the electron beam in the sensing area. The dose processing module comprises digital image processing means or matrix processing means able to compare the generated 2D image or 2D matrix with a pre-set 2D image or matrix for the purpose of detecting unacceptable discrepancies between the images or matrices.

In one or more embodiments a first set of exposed conductor surfaces are arranged in a common first plane, said first plane being a first sensor surface and is aligned with a first portion of the sensing area.

In one or more embodiments the electron beam emitter and the sensor device are arranged such, in relation to each other, that when the electron beam emitter passes over the sensor device a plane, corresponding to the surface of the electron exit window, is moved in a direction parallel to the first plane of the sensor device.

In one or more embodiments the sensor device and the electron beam emitter are arranged such in relation to each other that when the electron beam emitter passes the sensor device a distance in the range of 1-10 mm is formed between the plane of the electron exit window surface and the first plane of the sensor device.

In one or more embodiments the sensing area has a length in a first direction being larger than a longest extension of an area, along the first direction, passed by the electron beam, when the electron exit window is moved past the sensing area in a second direction being either perpendicular to the first direction or angled in relation to the first direction.

In one or more embodiments the exposed conductor surfaces of the first set are arranged one after the other along a line.

In one or more embodiments said line is aligned with the first direction.

In one or more embodiments a second set of exposed conductor surfaces are arranged in a common second plane, said second plane being a second sensor surface, being parallel to the first plane and spaced from the first plane in a direction substantially perpendicular to the plane of the electron exit window and away from said plane of the electron exit window, and being aligned with a second portion of the sensing area.

In one or more embodiments the exposed conductor surfaces of the second set are arranged one after the other along a line, said line being aligned with the first direction.

In one or more embodiments the support is connected to a voltage potential and is partly surrounding the conductors to form a plasma shield.

In one or more embodiments the voltage potential is ground potential.

In one or more embodiments each conductor is a pin arranged through a hole in the support, that the exposed conductor surface is formed by a surface in a first end of the pin, and that the second end of the pin is connected to an insulated electrical cable, which cable exits the support and connects to the current signal module.

In one or more embodiments each conductor is a pin arranged through a hole in the support, that the exposed conductor surface is formed by a surface in a first end of the pin, and that the second end of the pin exits the support and forms a portion of a male part of a shielded pin connector.

In one or more embodiments a female part of said shielded pin connector is adapted to be connected to said male part of said shielded pin connector. A cable from the female part of the shielded pin connector is connected to the current signal module.

In one or more embodiments the sensor device is located on the inside of a radiation shield and the current signal module is located on the outside of the radiation shield.

In one or more embodiments the irradiation device is provided in a filling machine for use in sterilization of packaging containers, and comprises a first position being a packaging container infeed point, and a second position being a packaging container outfeed point. Said electron beam emitter is adapted to perform a first movement from the first position to the second position, and during said first movement the electron beam emitter is adapted to be at least temporarily engaged with a packaging container for irradiating said packaging container, and said electron beam emitter is adapted to perform a second movement from the second position to the first position, and during said second movement the electron beam emitter is adapted to move past the sensor device such that the electron beam emitted from the electron exit window is adapted to be at least temporarily located within a sensing area of the sensor device.

In one or more embodiments said electron beam emitter is being arranged on a rotatable carrier. The carrier is adapted to let the electron beam emitter pass the packaging container infeed and the packaging container outfeed.

In one or more embodiments it comprises packaging container conveying means being adapted to convey the packaging container from said infeed to said outfeed synchronously with the rotation of the carrier and aligned with the electron beam emitter.

In one or more embodiments the packaging container conveying means being further adapted to displace the packaging container in relation to the electron beam emitter between a non-engaged position in which the packaging container and the electron beam emitter are not engaged with each other and an engaged position in which the packaging container and the electron beam emitter are fully engaged with each other.

In one or more embodiments it comprises more than one electron beam emitter.

In one or more embodiments the sensor device has a sensing surface made up of surface segments, each surface segment being a conductor.

In one or more embodiments the support is formed as box made of an electrically conductive material. The box is filled with an electrically insulating material.

In one or more embodiments the conductors are made of an electrically conductive material, for instance a metallic material.

In one or more embodiments the support is made of an electrically conductive material, for instance a metallic material.

In one or more embodiments the exposed surface of the conductor is formed by an axial surface in a first end of the pin.

In one or more embodiments a third set of conductor surfaces are arranged in a common third plane, said third plane being parallel to the first and second planes and spaced from the second plane in a direction substantially perpendicular to the plane of the electron exit window and away from said plane of the electron exit window.

In one or more embodiments the support is stepped and the first set of conductor surfaces is positioned on a first step and the second set of conductor surfaces is positioned on a second step.

In one or more embodiments the third set of conductor surfaces is positioned on a third step.

The invention also relates to a method for irradiating objects with electron beams. Said method comprises providing at least one electron beam emitter having an electron exit window, providing at least one sensor device for detecting a first dose control parameter of the electron beam, moving said electron beam emitter past the sensor device such that the electron beam emitted from the electron exit window passes within a sensing area of the sensor device, and exposing, to the electron beam, a conductor surface of at least one conductor of said sensor device.

In one or more embodiments the first dose control parameter is electrical current generated in each of the conductors and the method comprises the step of measuring said electrical current with a current signal module.

In one or more embodiments the method comprises the step of providing a dose processing module in communication with the current signal module.

In one or more embodiments the method comprises the step of collecting, by the dose processing module, first dose control parameter measurements made at different times, during the passage of the electron beam over the sensor device, to generate an image of the electron beam.

In one or more embodiments the method comprises the step of processing the first dose control parameter, in the dose processing module, together with second dose control parameters to create dose information comprising dose rate (kGy/s) per area unit of the electron beam delivered from the electron beam emitter in the sensing area.

In one or more embodiments the method comprises the step of sending a feedback signal to an irradiation device control module if the dose rate in one or several of the area units is not within an acceptable, pre-set dose rate range.

BRIEF DESCRIPTION OF THE DRAWINGS

In the following, presently preferred embodiments of the invention will be described in greater detail, with reference to the enclosed schematic drawings, in which:

FIG. 4b is a side view of the sensor device of FIG. 4a, FIG. 4c is a perspective view of the side and top of the sensor device shown in FIGS. 4a-4b, FIG. 15 is a top view of another embodiment of a sensor device according to the invention, FIG. 16 is a top view of yet another embodiment of a sensor device according to the invention, FIG. 21b is a bottom view of the sensor device of FIG. 21a, and FIG. 21c is a side view of the sensor device of FIG. 21a.

DETAILED DESCRIPTION OF A PREFERRED EMBODIMENT

Figure 1:
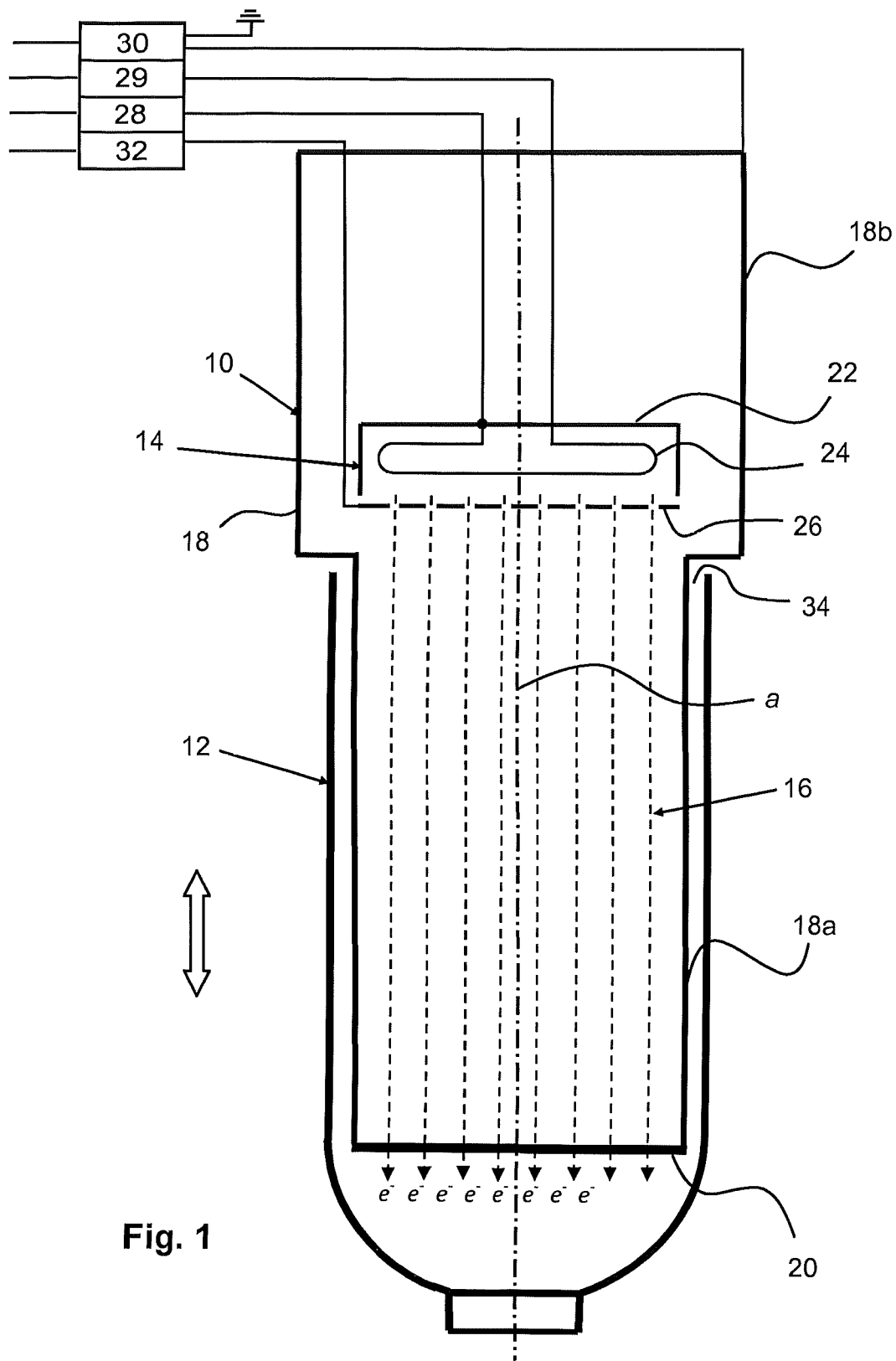
FIG. 1 is a packaging container and an exemplary electron beam emitter in a fully engaged sterilization position.

The irradiation device of the invention may be used for many purposes, one being sterilization of objects such as for example packaging containers, plastic pre-forms, plastic bottles and medical devices. In the following, and with reference to FIG. 1, an exemplary electron beam emitter 10 and the concept of electron beam sterilization will be briefly described. The object being sterilized is a ready-to-fill packaging container 12.

The electron beam emitter 10 comprises an electron generator 14 for emitting a substantially circular electron beam 16. The electron generator 14 is enclosed in a hermetically sealed vacuum chamber 18. Said vacuum chamber 18 is provided with an electron exit window 20.

The electron generator 14 comprises a cathode housing 22 and a filament 24. Optionally, the electron generator 14 also comprises a control grid 26. In use, an electron beam 16 is generated by heating the filament 24. When an electrical current is fed through the filament 24, the electrical resistance of the filament 24 causes the filament to be heated to a temperature in the order of 2000° C. This heating causes the filament 24 to emit a cloud of electrons. The electrons are accelerated towards the electron exit window 20 by means of a high-voltage potential between the cathode housing 22 and the exit window 20 (being the anode). Further, the electrons pass through the electron exit window 20 and continue towards the target area, i.e. in this case the inside of the packaging container 12.

The high-voltage potential is created by for example connecting the cathode housing 22 and the filament 24 to a power supply 28 and by connecting the vacuum chamber to ground 30. The filament also needs a second connection 29. The electron beam emitter 10 is generally denoted low voltage electron beam emitter if the voltage is below 300 kV.

For sterilization of packaging containers operating voltages in the order of 50-150 kV is conventionally used. In the disclosed design the accelerating voltage is in the order 90-100 kV. This voltage results in a kinetic (motive) energy of 95 keV in respect of each electron. By applying an electrical potential also to the control grid 26 the emission of electrons may be further controlled. If a separate and variable electrical potential is applied to the control grid 26 it makes it possible to use the control grid 26 for active shaping of the generated electron beam. For these purposes the control grid 26 may be electrically connected to a separate power supply 32.

The filament 24 can be made of tungsten. The grid 26, placed between the filament 24 and an electron beam exit window 20 provided with a number of openings and is used for diffusing the electron beam 16 into a more uniform beam, and for focusing the electron beam 16 towards the target area.

The emitter 10 is, as mentioned, further provided with an electron exit window 20. The window 20 is made of a metallic foil, such as for example titanium, and have a thickness in the order of 4-12 μm. A supporting net (not shown) formed of aluminum or copper supports the foil from inside the vacuum chamber 18. The electrons are exiting the vacuum chamber 18 through the exit window 20.

In this embodiment the vacuum chamber 18 is made up of two cylindrical bodies 18a, 18b with substantially cylindrical symmetry. An end of the first cylindrical body 18a is provided with the electron exit window 20. The diameter of said first body 18a is small enough to be inserted into the ready-to-fill packaging container 12, the cross section of said first body is dimensioned such that it can be guided through an opening 34 of the packaging container 12. The second body 18b is provided with the electron beam generator 14, and the diameter of said second body 18b is larger than the first body 18a. The diameter of the emitted electron beam 16, while still inside the emitter 10, is smaller than the diameter of the first body 18a.

In FIG. 1 the opening 34 of the packaging container is an open bottom end, which after filling will be sealed and folded to form a substantially flat bottom surface. It should however be understood that the opening may in other embodiments be arranged in the top of the packaging container, constituting a neck or spout portion of the packaging container. Such neck or spout portion will, after filling, be sealed by for instance a screw cap.

Figure 2A:
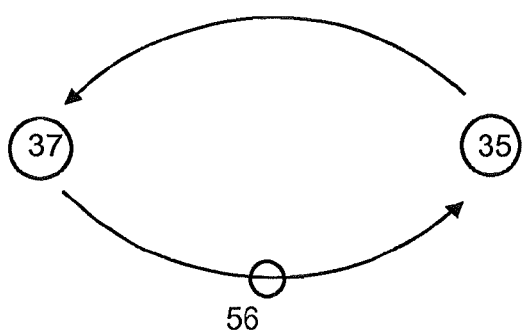
FIG. 2a is a first embodiment of the invention.

In FIG. 2a a first embodiment of the invention is shown, illustrating the general or conceptual idea of the invention. A packaging container is to be sterilized by an electron beam from an electron beam emitter in an irradiation device of a filling machine. In the irradiation device there is arranged at least one sensor device for measuring at least a first dose control parameter of the electron beam. The electron beam emitter has an electron exit window and is adapted to be movable from a first position 35 to a second position 37, and from the second position 37 to the first position 35. The positions 35, 37 are illustrated by circles in the figure, and the movement of the electron beam emitter is illustrated by arrows. Between the first position 35 and the second position 37 said electron beam emitter is adapted to be at least temporarily engaged with a packaging container for irradiating said packaging container. Between the second position 37 and the first position 35, the electron beam emitter is at least temporarily positioned with the electron exit window substantially in line with a sensor device 56, for allowing the sensor device 56 to measure the first dose control parameter of the electron beam of said electron beam emitter. The electron beam emitter is adapted to be transported simultaneously with the packaging container from the first position 35 to the second position 37, and the electron beam emitter sterilizes the packaging container during that transport. The electron beam emitter is then further transported from the second position 37 to the first position 35, and during that transport the electron beam emitter passes the sensor device 56. The electron beam emitter is in operation, i.e. emitting an electron beam, throughout the entire transport, i.e. from the first position 35 to the second position 37 and back to the first position 35.

The electron beam emitter is of the type described in relation to FIG. 1, but could alternatively be of another type suitable for sterilizing packaging containers of the bottle or pre-form type.

Figure 3B:
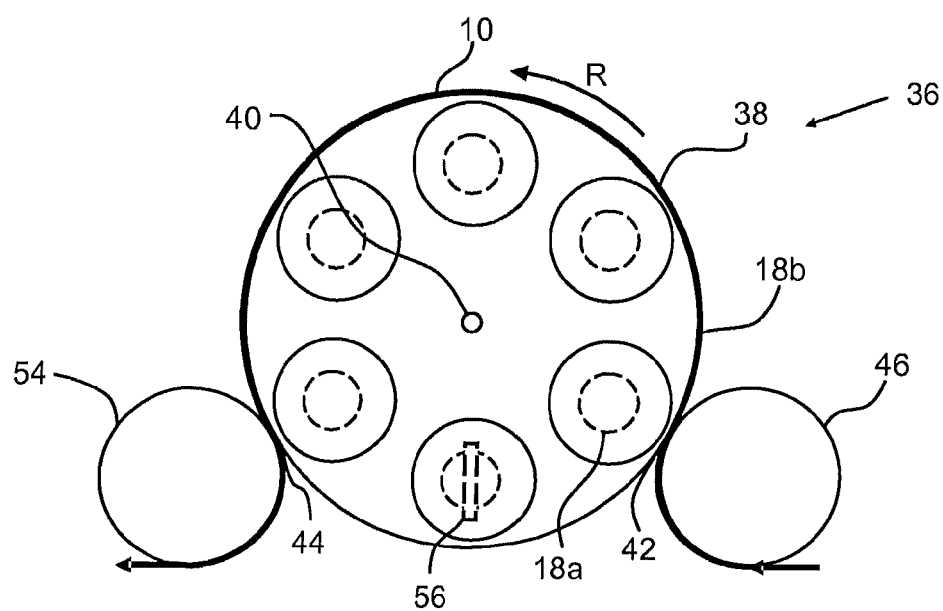
FIG. 3b is a view from above of the irradiation device of FIG. 3a, FIG. 4a is a top view of a sensor device according to the invention.

The first position 35 corresponds to a packaging container infeed point 42 (see FIG. 3b). At the infeed point the packaging container is starting to be moved relative the electron beam emitter in a vertical direction so that the electron beam emitter is started to be received in the opening (reference numeral 34 in FIG. 1) of the packaging container for sterilizing the packaging container. The second position 37 corresponds to a packaging container outfeed point 44 (see FIG. 3b). At the outfeed point 44 the packaging container has been or is about to be released from its engagement with the electron beam emitter, i.e. the packaging container is moved relative the electron beam emitter in the vertical direction, away from a position in which the electron beam emitter is received in the opening of the packaging container. The transport of electron beam emitter and packaging container from the first position 35 to the second position 37 is a packaging container sterilization cycle, whereas the transport of the electron beam emitter from the second position 37 to the first position 35 is an electron beam dose measurement cycle. Hence, dose measurement cycles are performed in between subsequent packaging container sterilization cycles.

Figure 2B:
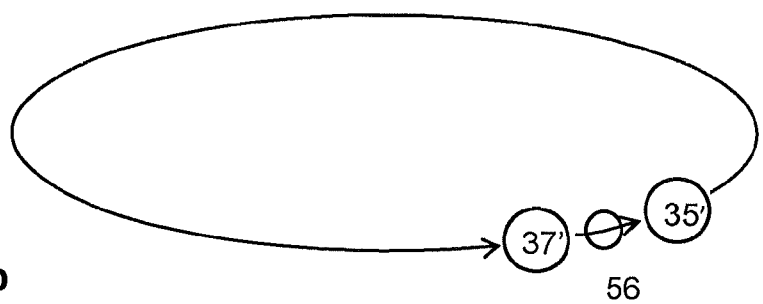
FIG. 2b is a second embodiment being a modification of the first embodiment.

FIG. 2b is showing a second, general embodiment being a slight variant of the first embodiment. The first position is a similar position as the first position 35 described above, but here denoted 35'. The second position is a similar position as the second position 37 described above, but here denoted 37'. The difference between the embodiments is that the packaging sterilization cycle involves a considerably longer transport distance and/or time than the dose measurement cycle.

Figure 3A:
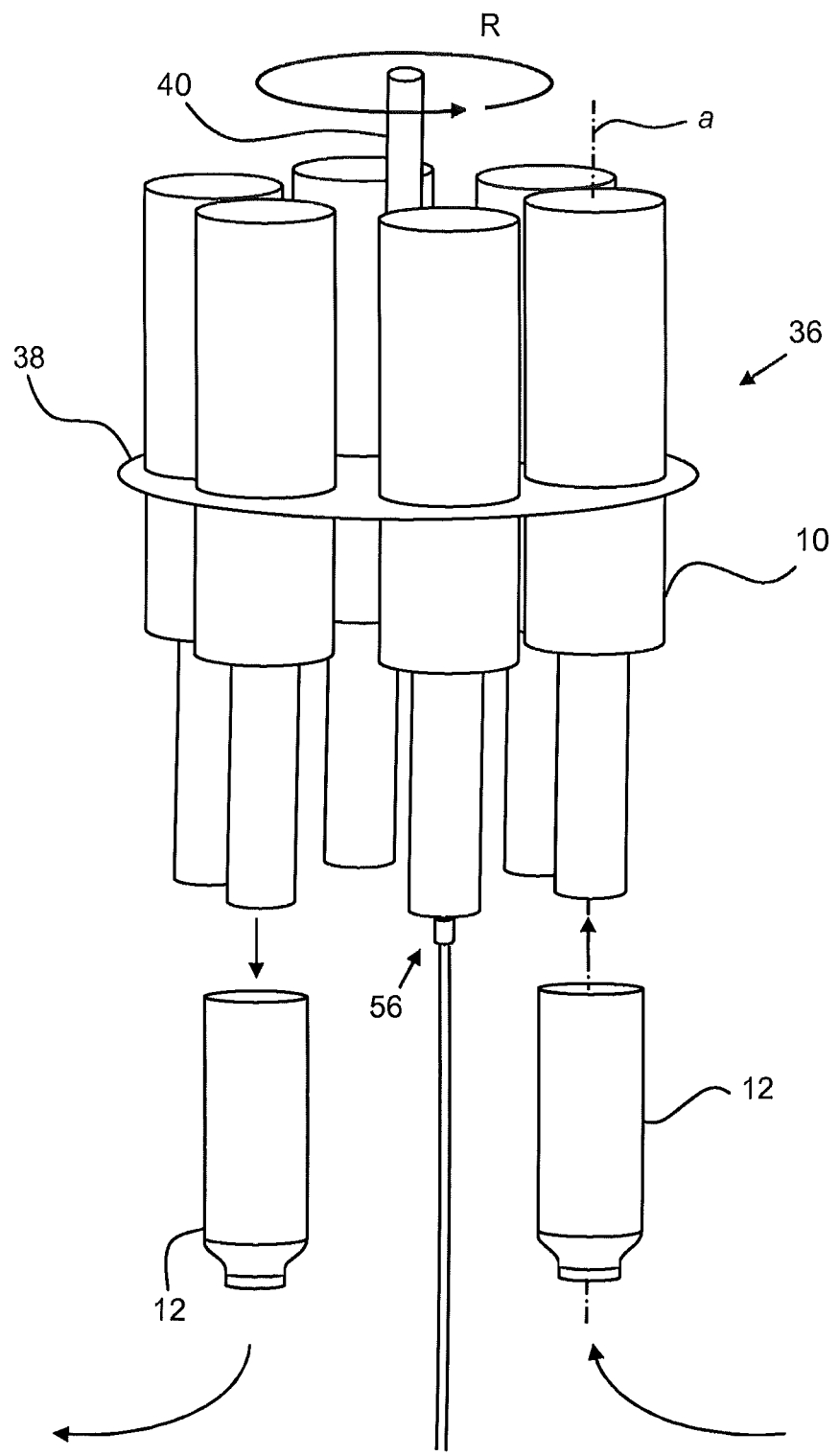
FIG. 3a is a perspective view of an irradiation device according to a third embodiment of the invention.

FIGS. 3a and 3b show a third embodiment of the invention, being a more detailed embodiment compared to the first two. The figures show an exemplary irradiation device 36 in which several above described electron beam emitters 10 are arranged. In this embodiment six emitters 10 are provided to a rotatable carrier 38. The rotatable carrier 38 is, in this embodiment, shaped as a wheel and is rotatable round a centre shaft 40. The direction of the rotation is illustrated by the arrow R and the rotatable movement is continuous. The emitters 10 are fixed to the carrier 38 so that they are being carried along when the carrier 38 rotates. The transportation of the packaging containers is made in a direction transversely to the longitudinal extension of the emitters 10.

The irradiation device 36 further comprises packaging container conveying means, not shown, being adapted to convey the packaging container 10 from the infeed point 42 to the outfeed point 44 synchronously with the carrier revolution movement and in alignment with the electron beam emitter 10. The packaging container 12 is moved synchronously with the electron beam emitter 10 and a longitudinal centre axis of the packaging container 12 is aligned with a longitudinal centre axis of the electron beam emitter 10, see the dashed-dotted line a in FIGS. 1 and 3*a*.

The packaging container conveying means is being further adapted to vertically displace the packaging container 12 in relation to the electron beam emitter 10. In the embodiment shown the electron beam emitter 10 is arranged stationary in the carrier 38 and cannot move towards the packaging container 12. The packaging container conveying means can displace the packaging container 12 between a non-engaged position in which the packaging container 12 and the electron beam emitter 10 are not engaged with each other and a engaged position in which the packaging container 12 and the electron beam emitter 10 are fully engaged with each other. At the infeed and outfeed points 42, 44 the packaging container 12 is positioned in the non-engaged position, i.e. not in engagement with the electron beam emitter 10. In this embodiment the infeed and outfeed points 42, 44 are similar to the first and second positions 35, 37 of the earlier described embodiments.

At the infeed point 42 the packaging containers 12 are supplied to the irradiation device 36 from an infeed wheel 46. Each packaging container 12 is aligned with a corresponding electron beam emitter 10. When the carrier 38 rotates, so that the electron beam emitter 10 and packaging container 12 rotates from the infeed point 42 to the outfeed point 44, the packaging container 12 conveying means displaces the packaging container 12 towards the electron beam emitter 10 so that the electron beam emitter 10 is received in the opening 34 of the packaging container 12 for sterilizing the packaging container 10. Somewhere between the infeed and outfeed points 42, 44 the packaging container 12 has been displaced such that the packaging container 12 is fully engaged with the electron beam emitter 10. The engaged position is shown in FIG. 1.

The packaging container conveying means is not the focus of this invention and will therefore not be described in detail. It may be arranged on the carrier 38, or on the electron beam emitters 10, or a combination thereof. It may alternatively be arranged separate from the carrier 38 but able to convey the packaging containers 12 synchronous with the carrier rotation. For example it may be arranged on an irradiation shielding device enclosing the carrier 38. The packaging conveying means is provided with packaging container gripping means that is adapted to grip the packaging container 12.

When reaching the outfeed point 44 a sterilization cycle, or irradiation cycle, of the packaging container 12 is completed and the packaging container 12 has been retracted from the engaged position back to the non-engaged position. Hence, the packaging container 12 is then ready to be fed out from the irradiation device 36 by means of an outfeed wheel 54 for further transfer to a filling device (not shown). Upon further rotation of the carrier 38, from the outfeed point 44 and back to the infeed point 42, the electron beam emitter 10 is not engaged with any packaging container 12 but is still maintained in operation, i.e. it still emitting the same electron beam. When reaching the infeed point 42 again a new sterilization cycle is commenced with a new packaging container 12 supplied from the infeed wheel 46.

The infeed and outfeed wheels 46, 54 are not the focus of this invention and will therefore not be described in detail. At the infeed point 42 the packaging container 12 is transferred from the infeed wheel 46 to the carrier 38 of the irradiation device 36. At the outfeed point 44 the packaging container 12 is transferred from the carrier 38 to the outfeed wheel 54 for further transport to a filling station.

The irradiation device 36 has been described in a schematic way. Only parts of the irradiation device 36 being involved in the invention has been described, but it is to be understood that the irradiation device comprises also additional parts such as drive units for driving the carrier 38 and the packaging conveying means, irradiation shielding enclosing the irradiation device 36 for securing that electrons and x-rays are not spread to the environment outside of the device, and aseptic barriers being either flow barriers or physical walls, or a combination of the two, for creating and maintaining satisfactory aseptic zones.

In the irradiation device 36 of the present invention the sensor device 56 is stationary arranged in the area between the outfeed point 44 and the infeed point 42, i.e. the area in which no packaging containers 12 are present in the irradiation device 36.

In the following, and with reference to FIGS. 4*a-d*, an exemplary sensor device according to the invention will be described.

Figure 4D:
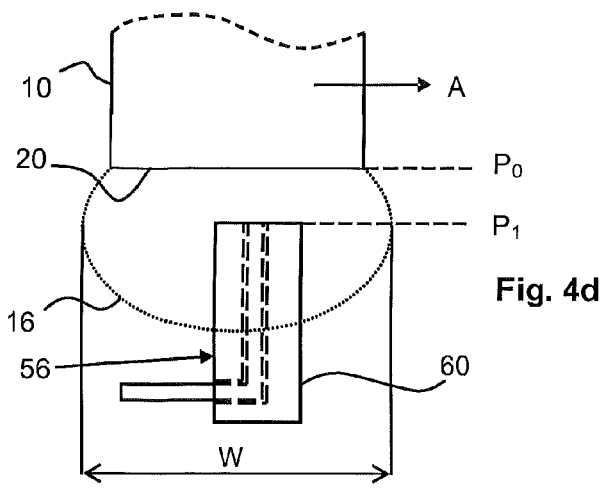
FIG. 4d is a side view of the sensor device of FIGS. 4a-c and an electron beam emitter.
Figure 8:
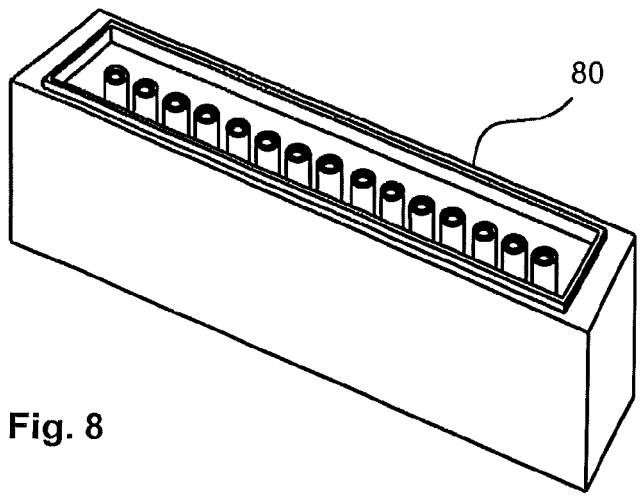
FIG. 8 is a perspective view of a female part of a pin connector.

The sensor device 56 is arranged in a stationary manner in the irradiation device 36, whereas the electron beam emitter 10 is adapted to move past the sensor device 56. This is illustrated in FIG. 4*d* and the movement of the electron beam emitter is shown as an arrow A. The electron beam emitter 10 and the sensor device 56 are arranged such, in relation to each other, that when the electron beam emitter 10 passes over the sensor device 56 a plane $P_0$, corresponding to the surface of the electron exit window 20, is moved in a direction parallel to a first plane $P_1$ of the sensor device 56. This is also seen in FIG. 8*d*. The two planes $P_0$ and $P_1$ are shown as dashed lines in the figure. Further, the electron beam emitter 10, of which only a portion is shown in FIG. 4*d*, is adapted to move such that the electron beam 16 emitted from the electron exit window 20 is passing within a sensing area 58 of the sensor device 56. The sensing area 58 will be described later on. The distance between the electron exit window plane $P_0$ and the first plane $P_1$ is the range of approximately 0.5-15 mm for an electron beam emitter of an operating voltage in the range of 50-150 kV. Preferably, a distance in the range of approximately 1-10 mm is used. The distance is preferably chosen depending on where on the electron beam, i.e. electron cloud, one want to measure. The electron beam exits the electron exit window in a quite narrow shape and as the electrons reach further away from the window they are scattering, which makes the electron beam become wider. In FIG. 4*d* it is seen that the plane $P_1$ is provided at a level similar to where the boundary of the electron beam has its largest width W. Alternatively, the sensor device is positioned such that the plane $P_1$ is very close to the electron exit window 20, i.e. closer than what is shown in FIG. 4*d*. In this case one measures on a less scattered electron beam. Scattering is usually a wanted effect in order to be able to fully reach the inside surface of a bottle, since the bottle diameter is larger than the diameter of the electron exit window. Generally, the scattering can be predicted by simulations or tested, and for a specified electron beam profile the scattering will look basically the same. Hence, it is possible to measure closer to electron exit window than at the largest width W of the electron beam.

The sensor device 56 comprises a support 60, see for example FIG. 4*a*. The support 60 is formed as a rectangular element and is made of a metallic material. Exemplary materials are aluminium or stainless steel. Any other metal can be used, or another material such as plastic material or a ceramic material optionally with an outside surface of metal. To avoid surface charges the support 60 is connected to a voltage potential. In an exemplary embodiment the voltage potential is ground potential. Hence, the support 60 is grounded (not shown).

The support 60 is provided with holes 62 adapted to accommodate conductors 64. The function of the conductors 64 is to conduct electrons, i.e. a current, and is therefore made of an electrically conductive material. The material may be for example any metallic material such as aluminium and stainless steel. Alternatively, an electrically conductive ceramic material can be used, or electrically conductive materials based on carbon or silicon.

In the embodiment shown in FIGS. 4a-4d the conductors 64 are formed as pins with a circular cross section. The holes 62 in the support 60 are also circular. The diameter of the pin is less than the diameter of the hole 62 in order to create a gap there between when the pin is inserted in the hole.

Said conductors 64 are electrically insulated from the support 60. The insulation, denoted 66, may be made of any electrically insulating material and is at least provided between the inside surface of the holes 62 in the support 60 and any surface of the conductors 64 being located inside the holes 62. In other words, the gap between the hole surface and the conductor is filled with electrically insulating material. Exemplary materials are ceramic materials. The conductor 64 may alternatively be coated with an insulating material, e.g. a non-electrically conductive ceramic coating or an anodically produced aluminium oxide coating (given that the conductor is made of aluminium).

Each conductor 64 has a conductor surface 68 being adapted to be exposed to the electron beam 16, i.e. being adapted to be at least temporarily in the path of the emitted electron beam 16 such that electrons from the beam can hit the conductor surface. In the embodiment shown in FIGS. 4a-4d there is a first set 70 of exposed conductor surfaces 68 arranged in the first plane $P_1$. The first plane $P_1$ is provided with the first set 70 of exposed conductor surfaces 68 is aligned with a plane constituting a first sensor surface, said first sensor surface being a top surface 72 of the support 60. It is an advantage to have the first set 70 of conductor surfaces 68 on the same level as the top surface 72 of the support 60 from a hygiene perspective since it will facilitate cleaning and prevent build-up of dust etc on the sensor device.

The exposed conductor surfaces 68 are provided within the sensing area 58 of the sensor device 56. The sensing area 58 is shown, for example in FIG. 4a, as a rectangle in dashed lines. The sensing area 58 is the area within which the electron beam 16 will pass. More specifically the sensing area 58 has a length in a first direction $D_1$. Said length is larger than a longest extension of an area, along the first direction, passed by the electron exit window or by the electron beam, when the electron exit window 20 is moved past the sensing area 58 in a second direction $D_2$. The second direction $D_2$ is either perpendicular to the first direction $D_1$ or angled in relation to the first direction $D_1$. In the following this is further explained by means of FIGS. 5a and 5b.

Figure 5A:
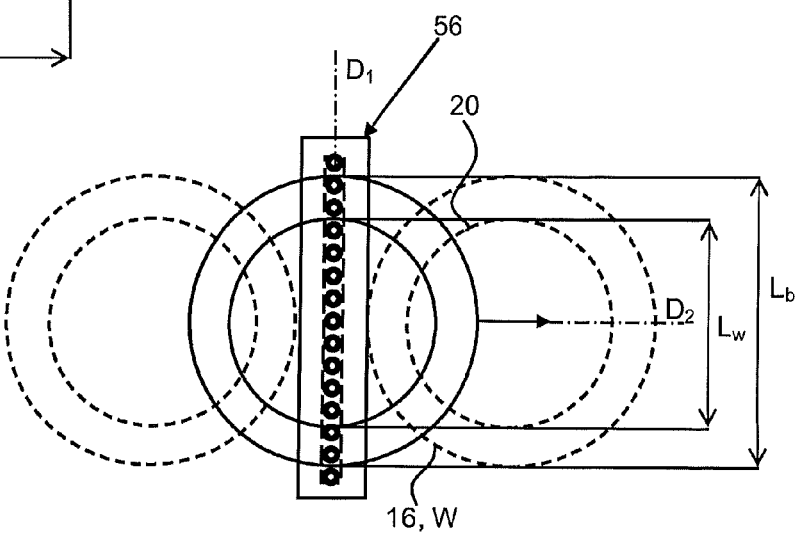
FIG. 5a is a top view of an electron beam and the sensor device.

In FIG. 5a the electron emitter is moved from left to right in the figure. Thereby the exit window 20 and the electron beam 16 are moved from left to right in the figure. The boundary of the electron exit window 20 is illustrated by a circle denoted with the same reference numeral (20). The boundary of the electron beam 16 is illustrated by a circle denoted with the same reference numeral (16) and defines the width of the electron beam at $P_1$. This may be the boundary at the "broadest" possible width, see W in FIG. 4d, or the boundary of a less scattered beam, depending on where the plane $P_1$ is located in relation to the electron exit window plane $P_0$. The movement of the electron exit window 20 is illustrated by the arrow A and is parallel to the second direction $D_2$, the latter being illustrated by a dash-dotted axis. A moment when the electron exit window is positioned right above the sensing area 58 is shown, but dashed circles to the left and right illustrate moments before and after. The first direction $D_1$ is illustrated by a dash-dotted axis. In this example the first direction $D_1$ is perpendicular to the second direction $D_2$. Hence, a longest extension $L_w$ of an area, along the first direction $D_1$, being passed by the electron exit window 20, will be similar to the diameter of the electron exit window 20. If one wants to measure over the entire electron electron exit window 20 it is therefore clear that the extension of the sensing area 58 along the first direction $D_1$ should be at least equal to the diameter of the electron exit window 20. In order to compensate for tolerances the extension $L_w$ should preferably be at least somewhat larger than the diameter of the electron exit window 20. A longest extension $L_b$ of an area, along the first direction $D_1$, being passed by the electron beam 16, will be similar to the broadest diameter W of the electron beam. If one wants to measure over the entire electron beam at the width W it is therefore clear that the extension of the sensing area 58 along the first direction $D_1$ should be at least equal to the diameter of the electron beam 16. Preferably, the extension of the sensing area 58 should be a bit longer than the diameter of the electron beam at width W.

Figure 5B:
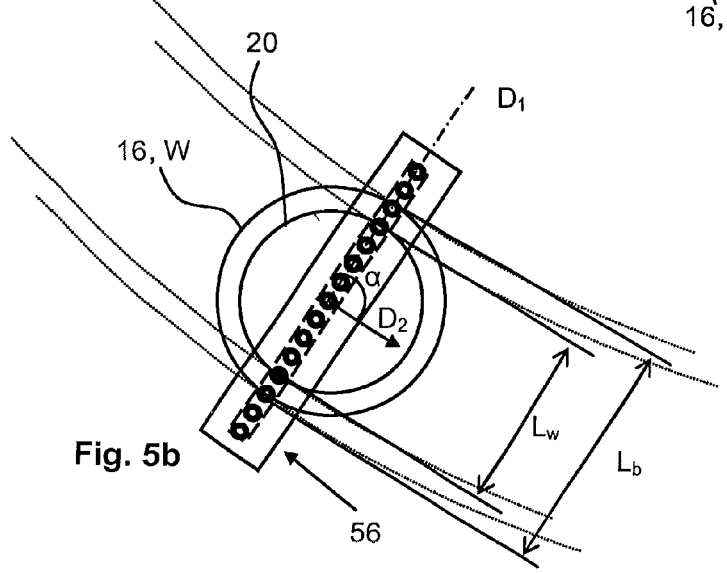
FIG. 5b is a view similar to that of FIG. 5a but with the electron beam shown in a different position.

Since the electron beam emitters are mounted on a rotatable carrier the electron exit window will pass the sensor device following along a curved path. This is to be illustrated in FIG. 5b. In FIG. 5b there is provided an angle α between the first direction $D_1$ of the sensor device 56 and the second direction $D_2$. The first direction $D_1$ will intersect the centre of the carrier. The second direction $D_2$ is parallel to the direction of movement, see arrow A, of the electron beam exit window 20. In this case arrow A illustrates the direction of the tangent of the curved path in a point being aligned with the centre of a conductor. Due to the angle α, a longest extension $L_w$ of an area passed by the electron exit window 20, seen along the first direction $D_1$, will be slightly longer than the actual diameter of the electron exit window 20. Dotted lines, aligned with the second direction $D_2$, show where the outer boundaries of the electron exit window 20 will cross the sensing area 58, and the longest extension along the first direction $D_1$ is shown as the length $L_w$. Similarly, a longest extension $L_b$ of an area passed by the electron beam 16, seen along the first direction $D_1$, will be slightly longer than the actual diameter of the boundary of the electron beam 16.

As can be seen in FIGS. 4a-4d the exposed conductor surfaces 68 in this embodiment are arranged one after the other along a line. The line is aligned with the first direction $D_1$. Exposed conductor end surfaces 68e are preferably provided at the very ends of the sensing area 58 in the first direction $D_1$ to capture the electron beam 16 also at the boundary of the electron exit window 20. The rest of the exposed conductor surfaces are provided equally distributed over the line, i.e. along the first direction $D_1$. This will give an even measurement of the electron beam 16.

Figure 7:
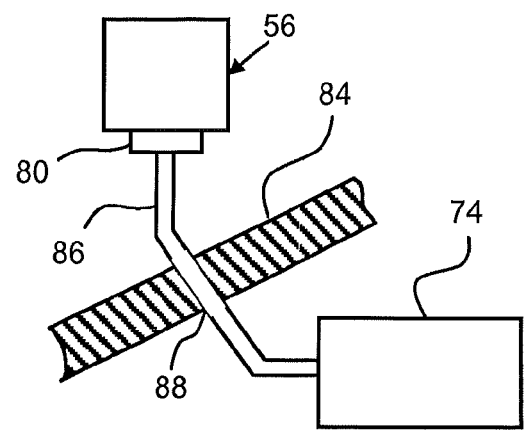
FIG. 7 is a view of a part of a radiation shield, the sensor device and a current signal module.

The irradiation device comprises a current signal module 74 (see FIG. 7). The current signal module 74 is connected to the sensor device 56 and is adapted to detect an electrical current in each of the conductors 64. This will be further described later on.

As previously mentioned each conductor 64 is formed as a pin and arranged through a corresponding hole 62 in the support 60. In the exemplary embodiment shown in FIGS.

4a-4d the exposed conductor surface 68 is formed by an axial surface in a first end of the pin. That surface is aligned with the first plane $P_1$ forming the top surface 72 of the sensing device 56. The pin extends through the hole 62 in the support 60. Further, a second end of the pin exits the support 60 and forms a portion of a male part 76 of a shielded pin connector. As can be seen in FIGS. 4a-4d the second end of the pin exits through a wall 78 of the support 60 being perpendicular to the first plane $P_1$, i.e. to the top surface 72 of the sensing device 56. In FIG. 4b dashed lines show the extension of the pins through the holes 62 of the support 60. As can be best seen in FIG. 4c the second ends of the pins together form the male part 76 of a shielded pin connector. A female part 80 of said pin connector will be described later on with reference to FIG. 8. The pin connector is of the type with a metal shield and is usually referred to as a "D-sub". The male part is sometimes referred to as the plug, and the female part is sometimes referred to as the socket.

Figure 6:
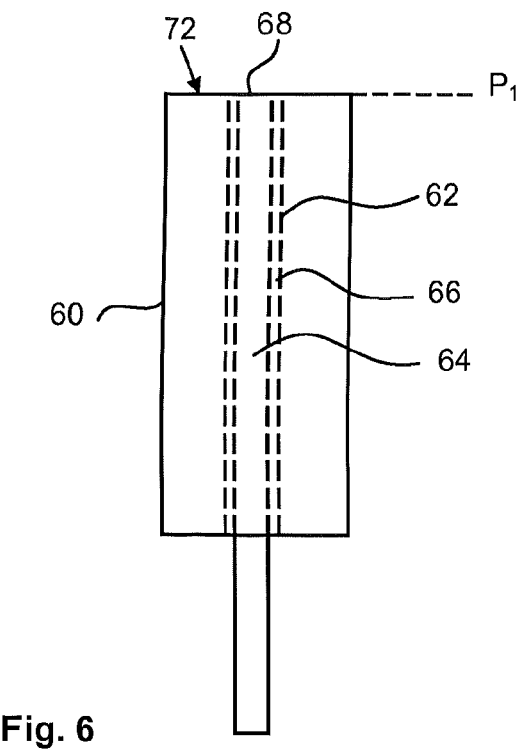
FIG. 6 is a side view of another embodiment of the sensor device.

In an alternative embodiment, shown in FIG. 6, the second end of the pin exits through a bottom wall 82 of the support 60, i.e. through a wall 82 being parallel to the top surface 72.

It has been described that the conductors 64 are insulated from the support 60 by insulation 66. Since the support 60 is connected to ground potential and partly surrounds the conductors 64, the support 60 acts as a plasma shield. Plasma electrons, which are of lower energy, are conducted away from the sensing area of sensor device. Hence, they cannot disturb the measurement by the sensor device. In the following, plasma and secondary electrons will be described. When an electron ($e^-$) emitted from the filament of the electron beam emitter travels towards the target, e.g. the packaging container, it will collide with air molecules. The emitted electrons can have sufficient energy to ionize the gas, thereby creating a plasma which contains ions and electrons. Plasma electrons are secondary electrons, or thermal electrons, with low energy compared to the electrons from the electron beam. The plasma electrons have randomised vector velocity and can only travel a distance which length is a small fraction of the mean free path for the beam electrons.

As previously mentioned the irradiation device 36 comprises a current signal module 74 for measuring currents created in the respective conductors 64. The electrical current is a first dose control parameter. The electrons of the emitted electron beam 16 hitting the exposed surfaces 68 of the conductors will create small currents in the conductors 64. By measuring each such current, by separate current meter devices in the current signal module, it is possible to obtain information about the electron beam intensity. The current meter device can be for example an ampere meter, or a resistor connected to for example an oscilloscope. Alternatively, other conventional current meter measurement devices may be used.

In FIG. 7 it is shown how the current signal module 74 and the sensor device 56 is interconnected. The sensor device is 56 placed inside a radiation shield. The emitters 10 need to be located within a radiation shield in order to prevent harmful radiation and x-rays to leak out of the irradiation device. A portion of the radiation shield is shown as wall 84 in FIG. 7. The current signal module 74 is located on the outside of the radiation shield. From the current signal module 74 there is provided a cable 86 in which free end there is provided the female part 80, i.e. the socket, of said shielded pin connector, see FIG. 8. The cable 86 extends through a hole 88 in the radiation shield. The hole 88 is illustrated as being straight, for simplicity, but it should be understood that it is in fact designed as a labyrinth. Any x-ray from the irradiation chamber should need to hit a wall of the radiation shield twice before being able to enter the environment outside the radiation shield. In this way the sensor device 56 and the current signal module 74 can be easily and stably connected to each other, and the current from each exposed conductor surface 68 can be securily transferred to the current signal module 74.

Figure 9:
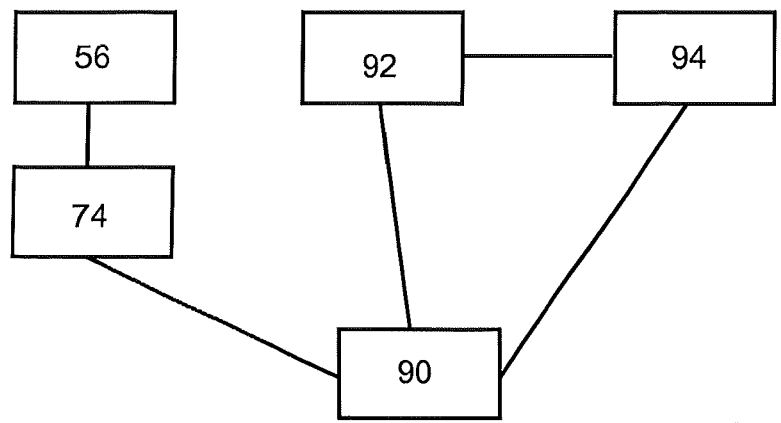
FIG. 9 is a block diagram of software modules according to the invention.

The current signal module 74 can continuously or intermittently register the current in each conductor 64 when the emitter 10 is passing, and feed the information, i.e. the first dose control parameter, to a dose processing module 90 for processing of the information. FIG. 9 illustrates that module and other modules being connected to each other and the sensor device 56. As can be seen from the figure the dose processing module 90 is in communication with an emitter control module 92. Said emitter control module 92 handles at least a first part of the second dose control parameters such as the current and voltage fed to the electron beam emitter, i.e. the current over the filament 24 of the electron beam emitter 10 and the voltage between the electron exit window 20 and said filament 24. This information is fed to the dose processing module 90. A second part of the second dose control parameters is handled by an irradiation device control module 94, which is part of a filling machine control module. This second part regards at least the position of the electron beam emitter in relation to the sensor device. This information is either fed via the emitter control module to the dose processing module, or directly to the dose processing module. Hence, all of these second control parameters are fed to the dose processing module 90. The second dose control parameters are processed together with the first dose control parameter, i.e. the currents, from the current signal module to create dose information comprising dose rate (kGy/s) per area unit of the electron beam delivered from the electron beam emitter in the sensing area. The meaning of dose rate per area unit will be further described later on.

Further, the dose processing module 90 is adapted to provide a feedback signal to the irradiation device control module 94 of the filling machine if the dose rate in one or several of the area units is not within an acceptable, pre-set dose rate range. A filling machine is a machine for manufacturing the packaging containers and that sterilizes, fills and seals them. The irradiation device forms the part of the machine performing the sterilization. The irradiation device control module 94 may be for instance be part of a PLC (Programmable Logic Controller) module of the filling machine.

The feedback from the dose processing module 90 to the irradiation device control module 94 is immediate and in case an improper dose rate is detected in any area unit of the electron beam in the sensing area, resulting in improperly sterilized packaging containers, action can be taken quickly. An advantage in this regard is that the electron beam is measured in between every sterilization cycle, and that therefore presence of improperly sterilized packaging containers may be discovered early on. This reduces the amount of packaging containers that will have to be discarded, compared to prior art daily dosimetry.

Further, as mentioned above, the dose processing module 90 is connected to the emitter control module 92. The emitter control module 64 can be used for controlling and adjusting for example the voltage and current being fed to the electron beam emitter 10. Hence, the voltage and current may be adjusted based on input from the dose processing module 90. This is useful in case it is discovered that more electrons need to be emitted to secure that correct sterilization is obtained during the available sterilization time.

The dose processing module 90 and emitter control module 92 can be further used to calibrate the electron beam emitters 10. Since all electron beam emitters 10 on the carrier 38 are measured by one and the same sensor device 56 the electron beams of the emitters 10 can be mutually compared. If the electron beams differ unacceptably between the electron beam emitters, the emitter control module 92 can adjust their voltage and current so that the dose rate per area unit of the electron beam emitters 10 become equal or at least become within an acceptable range.

The current signal module 74, the dose processing module 90, the emitter control module 92 and the filling machine control module 94 are software modules that can either be comprised in one hardware unit or separated and comprised in two or several hardware units. For example, the current signal module 74 and the dose processing module 90 may be one hardware unit.

Further, the above described irradiation device control module 94 is optionally connected to a device (not shown) for separating insufficiently irradiated packaging containers from sufficiently irradiated packaging containers. In such case the dose processing module 90 sends a signal to the irradiation device control module 94 that the packaging container 12 just being fed out was sterilized by an improperly operating emitter 10. The irradiation device control module 94 thereby sends a signal to the separation device to separate out that improperly sterilized packaging container. In that way it is secured that only properly sterilized packaging containers can proceed to filling. Alternatively, the irradiation device control module 94 is connected to a device (not shown) for re-sterilization of the improperly sterilized packaging containers. The device captures the faulty packaging containers at the outfeed and feeds them back to the infeed to allow them to have another sterilization cycle. Since the packaging containers may already have received some of the dose, the operating voltage of the emitter may need to be adjusted not to give the re-circulated packaging containers a too high dose. It is also needed to provide a device for accumulation of packaging containers. Since there is a continuous stream of packaging containers being fed into the irradiation device a re-circulating packaging container will obviously cause some problem. It will occupy one of the emitters so that a new packaging container cannot be fed into the irradiation chamber. The device for accumulation can accumulate the new packaging containers being refused entry into the irradiation device. At any appropriate time the device of accumulation can be emptied while the manufacturing of new packaging containers can preferably be stopped.

Figure 10:
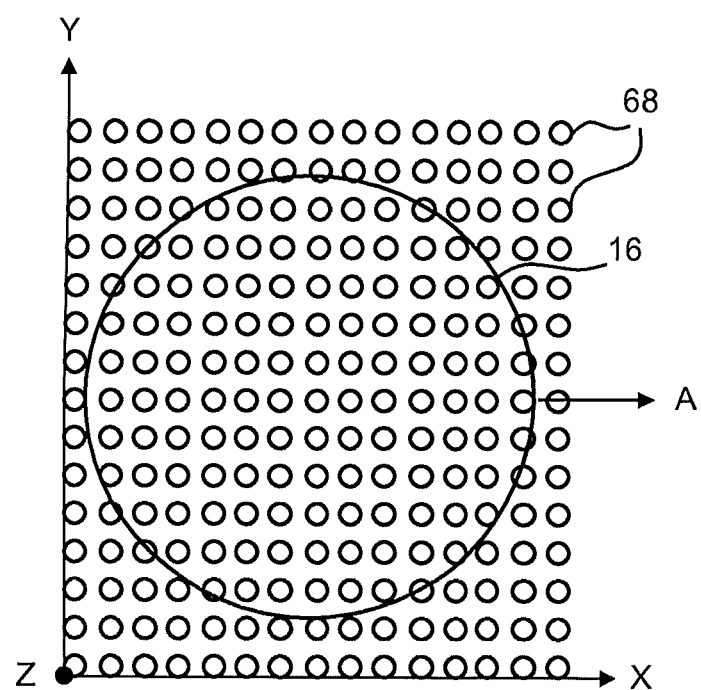
FIG. 10 is an illustration of area units.

In the following, and with reference to FIG. 10, dose rate per area unit will be discussed. The circle in the figure represents the boundary of the electron beam 16 in the first plane $P_1$ and the arrow A represents the direction of movement of the electron beam 16. Each area unit is determined by the area of the exposed conductor surface 68. One can see them as pixels. The number of pixels or area units in the sensing area is shown along an axis Y. Another axis X represents the sampling times, i.e. the number of times currents are measured and registered during the time the electron beam is passing over the sensing area. Every time a current measurement is made a new row of area units are added, thereby building a 2D image of measurement points/area units. This gives that one dose rate can be determined per area unit and hence give a mapping of the dose rates over the entire electron beam. Such dose rate mapping gives the beam shape or dose distribution. In fact, the image created can be said to be in 3D, since the current intensity in every area unit is measured, which gives values also along the z-dimension/axis (being perpendicular to the paper). These values may be illustrated as "topography" in the direction of the z-axis.

The current measurements are processed together with information about the position of the electron beam emitter, i.e. for every row of area units it is necessary to know in which position the electron beam emitter was.

Dose rate is the dose delivery per time unit or dose intensity. By measuring and controlling the dose rate it is possible to detect failures of the electron beam emitters, secure absorbed dose to the packaging containers and operate the electron emitters with the lowest possible load. In order for a packaging container to for example reach a sterilization level referred to as "commercially sterile" an absorbed dose of approximately 25 kGy (kilogray) is needed in every point of the interior surface of the packaging container. An electron beam emitter that is able to deliver a beam in which the amount, distribution and range of the electrons perfectly suits the packaging container surface profile is of course ideal in order to keep the sterilization time short and to keep a low load or stress on the electron beam emitter. Electron beam load or stress refers to the amount of emitted electrons in each point per time unit, i.e. the intensity; the dose rate (kGy/s). Ideally, the amount of emitted electrons should not need to be "oversized", but just as big as needed in order to obtain the desired dose in the packaging container. If an oversized amount is needed, due to for example improper intensity distribution, the electron beam emitter needs to be run with higher current and voltage to maintain the same sterilization time. In general, this negatively affects the lifetime. The higher the current and voltage needed to the drive the electron beam emitter, the shorter the lifetime will be.

If the electron beam emitter 10 is not delivering an ideal dose distribution it will take longer time, or require more from the electron beam emitter in terms of amount of emitted electrons, to obtain the dose all over the interior surface of the packaging container 12. If the electron beam distribution or intensity is really bad, having spots or areas where no or just a small amount of electrons reach the target, i.e. the packaging container surface, it may even be impossible to reach the dose in all areas of the packaging container during the sterilization time provided. If for example a part of the electron beam for some reason is deflected inside the electron beam emitter 10, with the result that some electrons do not reach through the electron exit window 20 but are instead hitting the inside surface of the emitter or getting stuck in the electron exit window, some areas of the packaging container 12 may not receive any dose. It may also be that only some electrons reach through the electron exit window 20, which would substantially increase the time until a satisfactory dose has been reached.

Figure 11:
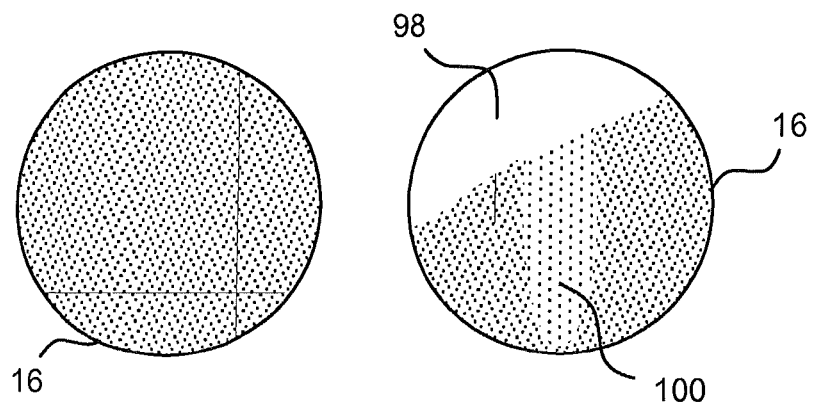
FIG. 11 is views of two examples of electron beam shape and intensity.

The above may be illustrated by FIG. 11. The left picture illustrates an exemplary, schematic, exemplary ideal distribution of an electron beam 16 (shown in 2D representation). Every electron is shown as a dot. The distribution is in this case even and the intensity, i.e. the dose rate, can be regarded as high. The right picture illustrates a corresponding exemplary electron beam 16 of a malfunctioning electron beam emitter. The beam has an irregular shape and an uneven distribution. Over an area 98 there are no electrons reaching the target, i.e. reaching the packaging container surface, and over another area 100 the intensity or amount of electrons is less than that of electron beam shown on the left side. A packaging container being irradiated with such electron beam emitter will not obtain the required dose, and will need to be discarded.

It should be noted that an ideal electron beam intensity and distribution may not always look like the one shown in FIG. 11. In fact, in some applications, it is instead desired to have an intensity and distribution not entirely even, but rotational symmetric and with an electron intensity and distribution not being the same along the radius of the window. In particular it may be desirable to use a ring beam when sterilizing packaging containers. A ring beam has no or just minor amounts of electrons emitted in the centre of the beam.

In order for the dose mapping to be correct and efficient there needs to be a calibration made between the dose processing module 90 and the different electron beam emitters 10 in the irradiation device, i.e. the dose processing module 90 needs to "learn" how the output from the different electron beam emitters looks like. The output of the electron beam emitters may not be totally similar, i.e. generally there are acceptable variations in output from one emitter to another. Hence, their outputs are initially measured by the sensor device 56 and stored as reference or baseline. This calibration can be made by simply rotating the carrier 38 one round so that all the electron beam emitters 10 pass the sensor device 56 once. If an electron beam emitter needs to be replaced by a new one, a separate calibration is made for the new electron beam emitter.

Once the calibration is made there are different ways of determining if the dose rate in one or several of the area units is not within acceptable, pre-set dose rate ranges. Either a present dose rate in an area is compared with a set value, for example a worst case value based on the baseline or reference, or it is checked that a present dose rate in an area is within an acceptable range around the baseline or reference.

Image recognition may be one way to determine discrepancies in one or several area units. In such case the dose processing module is provided with an image generation device adapted to generate a 2D image or 2D matrix based on the dose rate per area unit of the electron beam in the sensing area. Further, the dose processing module comprises digital image processing means or matrix processing means able to compare the generated 2D image or 2D matrix with a pre-set 2D image or matrix for the purpose of detecting unacceptable discrepancies between the images or matrices. Alternatively, said pre-set 2D image may be compared with two pre-set 2D images, each defining the upper and lower boundaries of acceptable values.

The size of the area units reflects how detailed the dose mapping will be, i.e. the "resolution" of the images. In the embodiment shown in FIGS. 4a-4d there are fifteen exposed conductor surfaces in a row. The distance between two subsequent conductor surfaces is 2.5 mm. The diameter of each exposed conductor surface is 1 mm. The diameter of the electron exit window is in the order of 30 mm. This is of course just exemplary numbers and dimensions, and depending on the application, the speed of the electron emitter movement, the size of the electron exit window and the desired level of details in the measurements other numbers and dimensions may be chosen. If less resolution is enough the distance between the conductor surfaces can be increased, and/or the number of surfaces can be decreased, and/or. Correspondingly, if a higher resolution is needed the distance between the conductor surfaces can be decreased, and/or the number of surfaces can be increased, and/or the number of times the sensor device 56 registers the currents can be decreased. If the size of the electron beam exit window is larger, for example having a diameter in the range of 100 mm or more, the diameters of the exposed conductor surfaces may of course be made larger, for example increased to diameters in the centimetre range rather than being in the millimetre range. Also the distance between the exposed conductor surfaces may be increased to distances in the centimetre range. For electron exit windows being smaller, for example having diameters in the range of 10-20 mm, the diameter of the exposed conductor surfaces may be made smaller. For example the diameter of the exposed conductor surfaces may be in the range of 0.05 mm-5 mm. A typical range of diameters for electron exit windows for use in sterilization of liquid food packaging containers and plastic bottle pre-forms is approximately 10-80 mm.

A dose control parameter measurement according to the present invention will necessarily not be able detect electric arcs that may be generated in the electron beam emitter. An arc may occur during a time period of less than a second, and cannot be detected by the sensor device unless occurring in the moment the electron beam emitter is passing the sensor device. However, if occurring during sterilisation of a packaging container, the result may be an unsterile packaging container. Therefore, it is advised to combine the dose control parameter measurement of the present invention with state of the art continuous measurements of voltage and current in the electron beam emitter. The current over the filament is continuously measured (comparison of current fed to the filament and current leaving the filament) and the voltage, i.e. the electric potential, between the electron exit window and the filament is continuously measured. An arc would result in a short, temporary, detectable fluctuation of the voltage and/or current. The measured values of current and voltage are processed by the emitter control module 92 and feedback is sent to either the dose processing module 90 or directly to the irradiation device control module 94.

A further advantage with the invention, if combined with the above mentioned current and voltage measurement, is that it can be utilized for detecting sensor device failure. If the voltage and current monitoring of the electron beam emitters show acceptable values but the feedback signal from the dose processing module 90 suddenly shows discrepancies for all the electron beam emitters, it is likely that the sensor device 56 itself operates faulty. Hence, it can be used for detecting sensor device 56 failure.

A further advantage with the invention is that it can be used to predict when it's time to replace the electron beam emitters. The images or matrices can be analysed more deeply to find single points in which there is a discrepancy, indicating deposit or dirt on the electron exit window or filament wear. Further, the amount of emitted electrons in relation to the current and voltage supplied to the emitter may be monitored over time. This is to be able to detect any slow decrease in the amount of electrons emitted although supplying the same current and voltage. Such may for example be an indication of filament wear. The information can be used to calculate an approximate expected lifetime.

Figure 12:
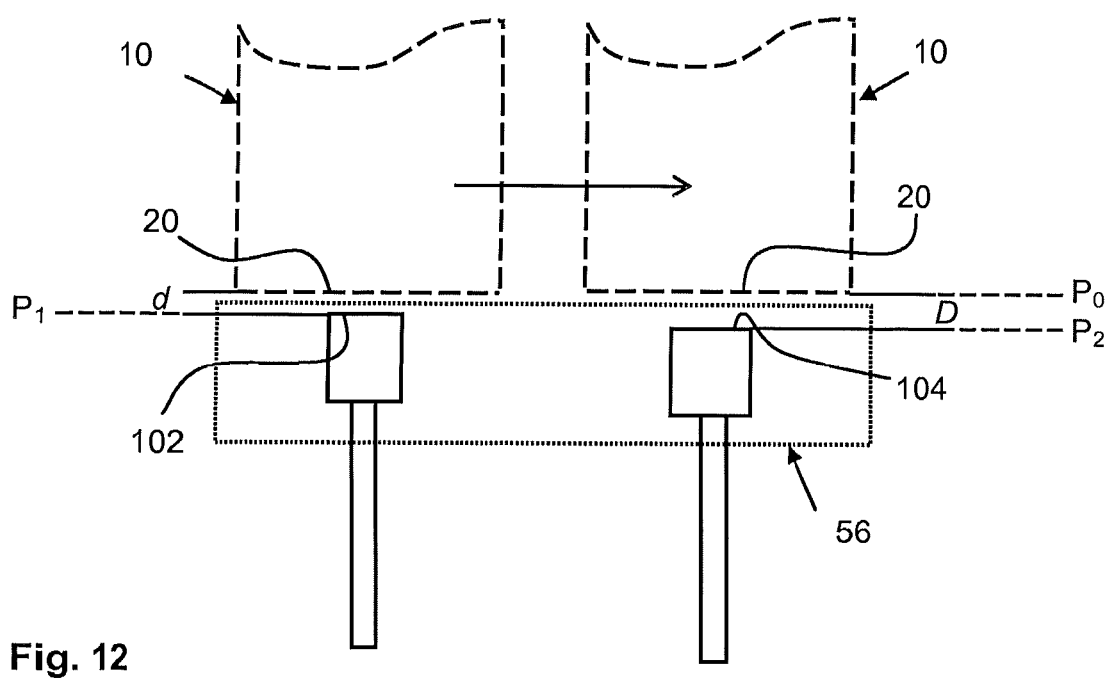
FIG. 12 is a side view of another sensor device of the invention.

FIG. 12 shows another embodiment of a sensor device according to the invention. Said sensor device 56 comprises a first sensor surface 102 and a second sensor surface 104. The sensor device 56 is shown in FIG. 12 together with dashed-lined boxes representing a passing electron beam emitter 10. The sensor surfaces 102, 104 are being arranged on two different levels in relation to the plane $P_0$ of the electron exit window 20 of the electron beam emitter 10. Hence, the two surfaces 102, 104 have different distances to the electron exit window 20. A larger distance D is formed between the electron exit window 20 and the second sensor surface 104, when in line with each other, than a distance d formed between the electron exit window 20 and the first sensor surface 102, when in line with each other.

The distance between the first sensor surface 102 and the second surface 104 is in the range of 5-20 mm. Hence, the larger distance D is the sum of the smaller distance d plus a distance in the range of 5-20 mm.

Generally, the distance between the two sensor surfaces 102, 104 needs to be matched with the acceleration voltage. In case of a relatively higher acceleration voltage, for instance 150 kV, the electrons will reach farther than in the case of a relatively lower acceleration voltage, for instance 95 kV. For the higher acceleration voltage the distance between the sensor surfaces 102, 104 may be made longer than in the case of the lower acceleration voltage. For the higher voltage a distance of 5-20 mm may be chosen, whereas in the case of the lower acceleration voltage a distance in the order of 5-10 mm is better.

Figure 13:
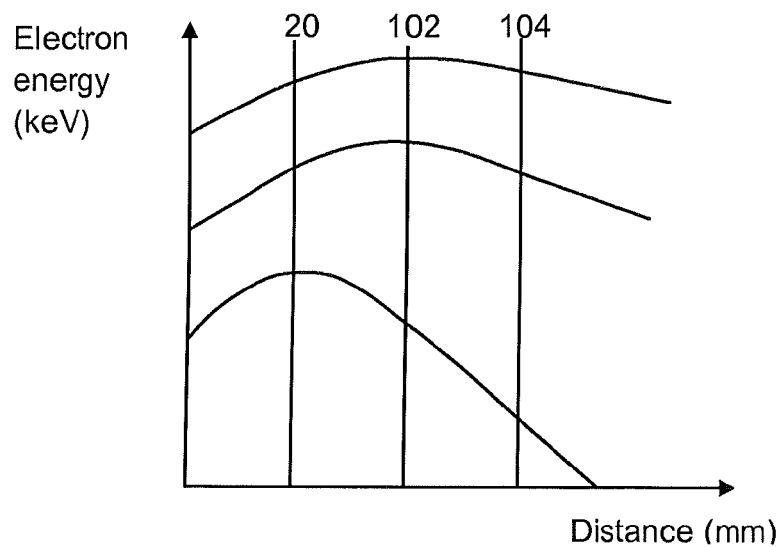
FIG. 13 is an illustration showing general electron energy distribution curves.

By arranging the sensor surfaces 102, 104 on two different levels in relation to the electron exit window 20, the electron energy distribution may be assessed, which is useful when assessing the dose distribution in a packaging container. FIG. 13 shows three graphs being different general electron energy distribution curves A-C. The y axis shows the electron energy level (keV) and the x axis shows the electron travelling distance (mm). Curve A shows the typical energy distribution for a case in which the initial electron energy is low. A relatively large amount of energy will be absorbed in the electron exit window 20. After passing the electron exit window 20 the electron energy will quickly decrease, which leads to a steep inclination of the energy distribution curve between the first sensor surface 102 and the second sensor surface 104. In a case where the initial electron energy is instead high, the curve will typically look like curve C. In this case relatively little energy is absorbed in the electron exit window 20, and the curve inclination between the first sensor surface 102 and the second sensor surface 104 is flat. Curve B shows the energy distribution of an intermediate initial electron energy, and the inclination between the first and second sensor surface 102, 104 is not as steep as in curve A, but not as flat as in curve C. By measuring the energy of the electrons with both sensor surfaces 102, 104 the inclination of the actual energy distribution curve can be assessed. For a properly working emitter 10 the inclination angle will not change over time. However, if it is changing, gradually or abruptly, it can be concluded that something has happened, for example there can be dirt or deposit building up on the electron exit window, or there can be a deviation in the acceleration voltage.

Figure 14A:
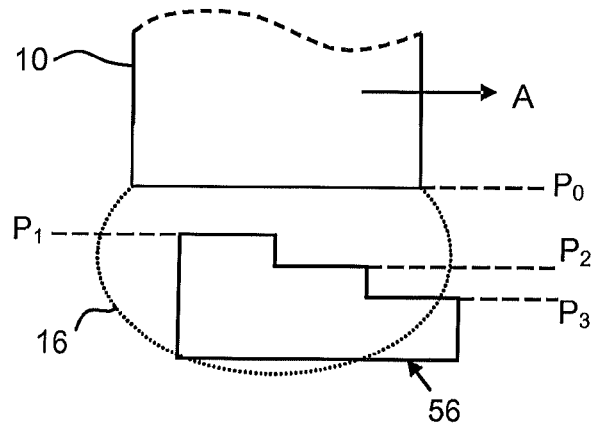
FIG. 14a is a side view of a stepped sensor device.
Figure 14B:
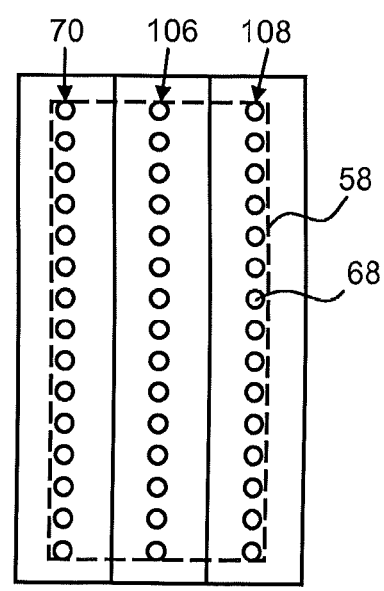
FIG. 14b is a top view of the stepped sensor device of FIG. 14a, FIG. 14c is a perspective view of the sensor device of FIGS. 14a and 14b.

A sensor device 56 with two sensor surfaces 102, 104 has been described in general in relation to FIG. 12. In FIGS. 14a-14c another embodiment is shown which is based on the sensor shown in FIGS. 4a-4d, but which is provided with additional sets of exposed conductor surfaces.

The sensor device comprises a second set 106 of exposed conductor surfaces 68. The second set 106 is arranged in a common second plane $P_2$, being similar to the previously described second sensor surface 104. Said second plane $P_2$ is parallel to the first plane $P_1$ and spaced from the first plane $P_1$ in a direction substantially perpendicular to the plane $P_0$ of the electron exit window 20 and away from said plane $P_0$ of the electron exit window 20. This is best seen in FIG. 14a. Having two sets of exposed conductor surfaces 70, 106, on two different levels, are often enough for assessing the electron energy distribution.

However, in this embodiment, also a third set 108 of conductor surfaces 68 is provided such that a more detailed assessment can be made. The conductor surfaces 68 of the third set 108 are arranged in a common third plane $P_3$. Said third plane $P_3$ is parallel to the first and second planes $P_1$, $P_2$. Further, it is spaced from the second plane $P_2$ in a direction substantially perpendicular to the plane $P_0$ of the electron exit window 20 and away from the plane of the electron exit window 20. The second and third sets 106, 108 of conductor surfaces 68 are similar to the first set 70 and will not be further described.

To accommodate all three sets 70, 106, 108 of exposed conductor surfaces the support 60 can be designed in a stepped way. As can be seen from FIGS. 14a-14c the first set 70 of conductor surfaces is positioned on a first step 110, the second set 106 of conductor surfaces is positioned on a second step 112 and the third set 108 of conductor surfaces is positioned on a third step 114. The height of each step, which corresponds to the distance d in FIG. 12, is similar. However, it is to be understood that the height may differ.

The sensing area 58 is in this embodiment formed by three portions, one first portion covering the first set 70 of exposed conductors, one second portion covering the second set 106 of exposed conductor surfaces and one third portion covering the third set 108 of exposed conductor surfaces.

A line X is added to FIG. 14b to illustrate that the sets are arranged aligned with each other, i.e. that an exposed surface from the first set 70 is arranged aligned with corresponding exposed surfaces of the second and third sets 106, 108. Further, the sets are parallel with each other and aligned in the first direction. Furthermore, the steps are preferably long in a direction along line X, such that the sets of exposed conductor surfaces are separated from each other. This is to avoid shadowing effects of the electron beam 16 within the sensor device, i.e. that any portion of the electron beam is shadowed by physical portions of the sensor device.

Figure 18:
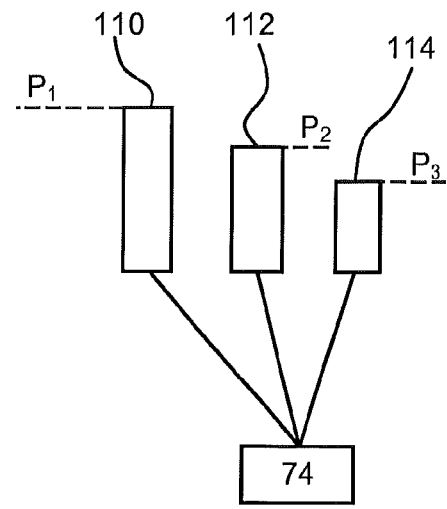
FIG. 18 is a side view of another embodiment of the sensor device shown in FIGS. 14a-14c.

In FIG. 18 there is shown a modification of the embodiment described above in relation to FIGS. 14a-14c. This embodiment will also eliminate any risk of shadowing effects. The three portions of the sensing area 58 are physically separated. Alternatively, three separate sensor devices of the type described in relation to FIGS. 4a-4c are used and positioned as shown in FIG. 18. In both cases the three sets of exposed conductor surfaces are positioned on different levels compared to the plane $P_0$ of the electron exit window. The different levels correspond to the earlier described first, second and third planes $P_1$, $P_2$ and $P_3$. The sets of exposed conductor surfaces are preferably connected to the same current signal module, as shown in the figure.

Figure 19:
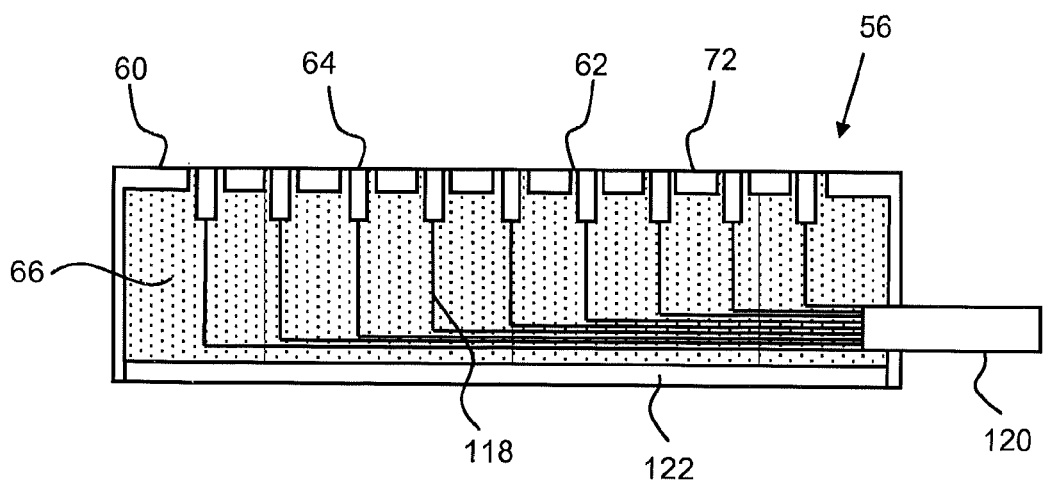
FIG. 19 is a top view of another embodiment of the sensor device.

Another sensor device embodiment is shown in FIG. 19. The principle for this sensor device is the same as that of FIG. 4a-c. It has conductors 64 in the shape of pins being provided in holes 62 on a top surface 72. The difference is that in this embodiment a D-sub connector solution is not used. Instead each pin is soldered to an insulated electrical cable 118. Said cables 118 are gathered in one larger insulation forming a cable 120 exiting the support 60. The exit of the cable 120 is positioned on a side surface. The support 60 is a hollow box made of a metallic material such as for instance stainless steel. The empty space inside the box is filled with an electrically insulating material 66. Said insulating material is also filling the gap between the holes 62 and the conductors 64. The electrically insulating material is any conventional material, for instance a ceramic material that may be poured in liquid form into the box and which is then subsequently cured. To facilitate mounting of the pins and cables the box has an opening in the bottom surface. The opening is optionally closed with a cover 122.

Although the present invention has been described with respect to a presently preferred embodiment, it is to be understood that various modifications and changes may be made without departing from the object and scope of the invention as defined in the appended claims.

In the description the electron exit window 20 of the electron beam emitter 10 has been shown as having a circular shape. However, it is to be understood that another shape is of course possible. For example the electron exit window may be oval, annular (i.e. doughnut-shaped), rectangular, triangular, quadratic, pentagonal, hexagonal or octagonal depending on in which application it is used.

Figure 17:
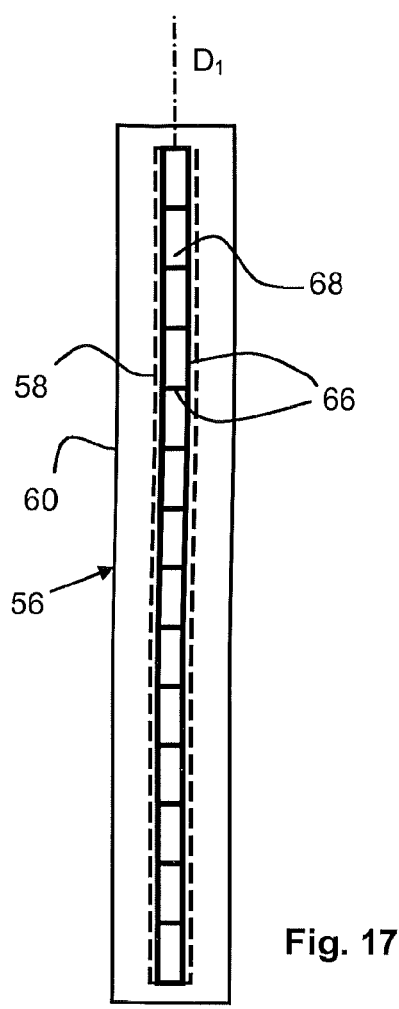
FIG. 17 is a top view of another embodiment of the sensor device shown in FIG. 15.

In the embodiment described in FIGS. 4a-d the cross section of the conductors are circular. However, any other cross section is of course possible. For example the cross section may be oval, rectangular, quadratic, pentagonal, hexagonal or octagonal. FIG. 15 shows conductors being rectangular. The rectangular cross section can be located such that the longest side is aligned with the first direction, as shown, or such that the longest side is aligned with a direction being perpendicular to the first direction. In FIG. 17 another slightly modified embodiment is shown. Here the distance between the exposed conductor surfaces 68 have been minimized in order to increase the resolution of the dose mapping. Only insulation is present between the conductors in the first direction $D_1$.

FIG. 16 shows an alternative embodiment in which the first set 70 of exposed conductor surfaces comprises two lines of conductor surfaces. One of the lines is offset the other line a distance in the first direction $D_1$ being half the distance between the centres of two subsequent exposed conductor surfaces 68. Alternatively it can be described that the exposed conductor surfaces of the first set forms a zig-zag-shaped line. This embodiment also gives a detailed dose mapping since the two lines together reduce the area that is not measured. In fact, if the sampling time is kept very short this arrangement of conductors gives a very detailed dose mapping.

The embodiments in FIGS. 14a-14c can be combined with the embodiment shown in FIG. 16 such that for example one or two of the sets of exposed conductor surfaces are offset the other(s).

Figure 21A:
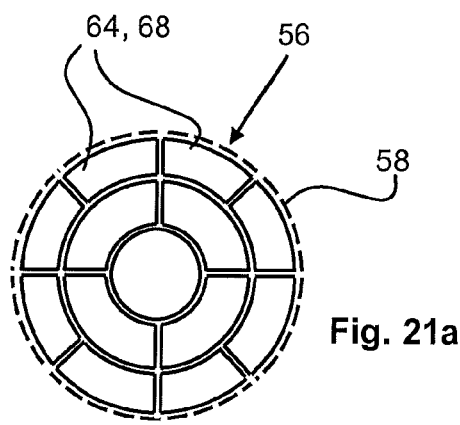
FIG. 21a is a top view of a surface-type of sensor device.
Figure 21B:
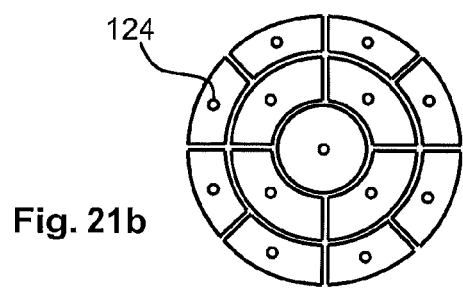
Figure 21C:
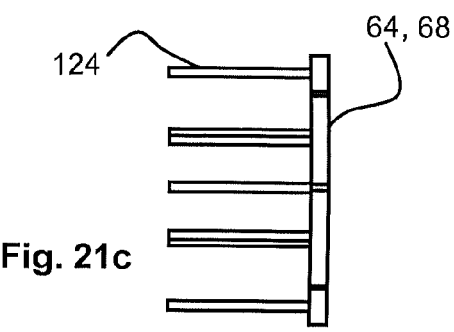

The exemplary carrier in FIGS. 3a-3b embodiment is a circular wheel but it should of course be understood that the carrier could alternatively be an endless conveyor of any shape. Further, the carrier is rotated with a continuous movement. Alternatively, the carrier may instead rotate intermittently. The type and/or position of the sensor device need to be chosen accordingly. If the electron emitter is paused aligned with the sensor device, the sensor device is preferably of the surface type of sensor, i.e. a sensor device being able to measure the entire electron beam in one instant. A surface type of sensor may be used also in an irradiation device with continuously moving emitters, like the device shown in FIG. 3a. In the following, and with reference to FIG. 21a-c, an embodiment of a surface type of sensor device will be described. Features having the same function as in the previously described sensor devices will be denoted with the same reference numerals. The sensor device 58 comprises conductors 64. The conductors 64 in this embodiment are shaped as surface segments which together form a sensing surface 58. In this embodiment there is provided a centrally positioned circular surface segment, a first annular surface segment coaxially positioned outside of the circular surface segment, and a second annular surface segment coaxially positioned outside of the first annular surface segment. Each of the first and second annular surface segments are divided in equally sized sub-segments. The sensing surface 58 has a shape and size being at least a bit larger than the boundary of the electron beam to be measured. The conductors are made of an electrically conductive material such as a metal or electrically conductive ceramic material, carbon or silicon. One insulated electrical cable 124 is soldered to each of the surface segments. Electron hitting the surface segment will give rise to a current in the cable 124. Each cable 124 is connected to the current signal module 74. Between the conductors 64 there is provided insulation material (not shown) for electrically insulating the conductors from each other. The insulation may act as support. When using a surface sensor the measurement is made slightly different compared to a line type of sensor. With a surface sensor a "snap shot" measurement is made in an instant when the sensor and the electron exit window is aligned with each other, i.e. when an imagined centre axis (extending perpendicular to the sensor surface) of the sensor surface is aligned with a centre axis (extending perpendicular to the electron exit window) of the electron exit window. At that point the boundary of the electron beam to be measured should be located within the sensing area 58 of the sensor device 56. The snap shot measurement gives the beam intensity in each surface segment, and together the surface segments can be used to make a 2D, or 3D, image of the dose rate, based on information about the position of the electron beam emitter and the voltage and current provided to the electron beam emitter. Each surface segment is the previously described are unit, and by varying the number and size of the surface segment the resolution can be varied. Many small surface segments give a more detailed resolution than few larger surface segments.

Also with the surface type of sensor device a calibration is made. Snap shots are taken of all the electron beam emitters of the carrier and are stored as reference or baseline.

In the disclosed emitter 10 the accelerating voltage is in the order of 95 kV. However, the invention should not be limited to an acceleration voltage in that order. It may be any voltage within the interval 50-300 kV depending on the application, for example an acceleration voltage of 150 kV is common in the PET bottling industry. Depending on the acceleration voltage a suitable sensor device 56 is chosen.

In the described embodiments the sensor device 56 is stationary positioned, whilst the electron beam emitter is adapted to be moved past the sensor device 56 so that the measurement can be performed. An alternative is that the sensor device 56 is also made movable. The sensor device 56 may be moved synchronously, and in alignment, with the electron beam emitter during at least a portion of the electron beam dose measurement cycle. Such would increase the time available for measurement.

Further, in the embodiments described the electron beam emitter and the sensor device are stationary in the vertical direction, i.e. none of them is adapted to be movable in the vertical direction, i.e. in relation to each other. In alternative embodiments at least one of the sensor device 56 and the electron beam emitter is movable in relation to each other in the vertical direction to provide them in a position suitable for dose parameter measurement. Either one of them is movable in relation to the other, or both are movable a distance each. A relative movement in the vertical direction is necessary if the design of the irradiation device, for some reason, does not otherwise provide for a gap between the electron exit window 20 and the top surface 72 in the range of approximately 1-10 mm.

In FIG. 9 the current signal module 74 is seen as being physically separated from the dose processing module 90.

However, it is to be understood that the two may be accommodated in one module.

Figure 20:
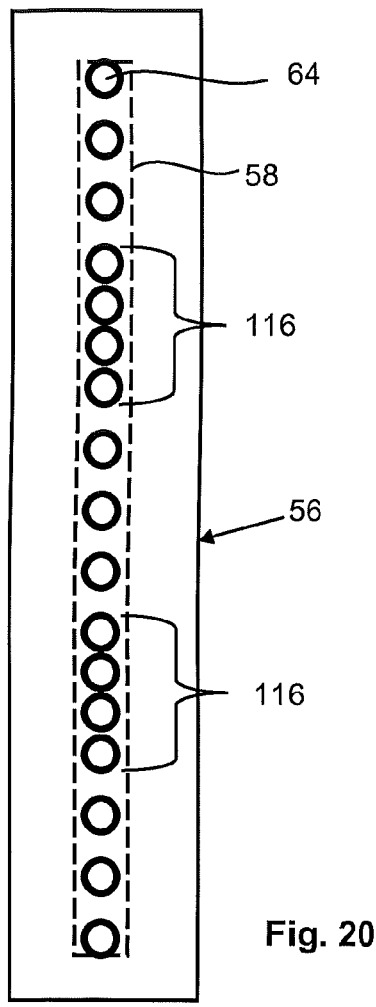
FIG. 20 is a cross section of yet another embodiment of the sensor device.

In the sensor device embodiment shown in FIGS. 4a-d the conductor surfaces are equally distributed. However, if one would like to focus the measurement over certain areas of the electron beam it is to be understood that more exposed conductor surfaces 68 may be provided in those focus areas than in the less interesting areas, i.e. the concentration of conductor surfaces may be increased over the focus areas. This is illustrated in FIG. 20. The focus areas are denoted 116.

In the embodiments shown the sensor device has been shown with the exposed conductor surfaces being in the same level as the support, i.e. the top surface is flat. If it is desired to considerably increase the exposed conductor surfaces without considerably increase the size of the sensor device it is possible to let the pins extend out of the support in the sensing area. Thereby, the top surface will not be flat and the electron-catching surface will be larger.

The invention claimed is:

1. Irradiation device for irradiating objects with electron beams, the irradiation device comprises
    at least one electron beam emitter having an electron exit window,
    at least one sensor device for detecting a first dose control parameter of the electron beam, wherein,
    the electron beam emitter is adapted to move past the sensor device such that the electron beam emitted from the electron exit window passes within a sensing area of the sensor device, and the sensor device comprises more than one conductor each having a conductor surface in the sensing area of the sensor device, which conductor surface is adapted to be exposed to electrons of the electron beam.

2. The irradiation device according to claim 1, wherein the first dose control parameter is electrical current and wherein the sensor device is connected to a current signal module adapted to measure any electrical current from each of the conductors,
    the current signal module is in communication with a dose processing module, and
    the dose processing module is adapted to collect first dose control parameter measurements made at different times, during the passage of the electron beam over the sensor device, to generate an image of the electron beam.

3. The irradiation device according to claim 2, wherein the first dose control parameter is processed, in the dose processing module, together with second dose control parameters to create dose information comprising dose rate (kGy/s) per area unit of the electron beam delivered from the electron beam emitter in the sensing area, and wherein the second dose control parameters comprise current and voltage fed to the electron beam emitter and position of the electron beam emitter in relation to each conductor of the sensor device.

4. The irradiation device according to claim 3, wherein the support is connected to a voltage potential and is partly surrounding the conductors to form a plasma shield.

5. The irradiation device according to claim 3, wherein each conductor is a pin arranged through a hole in the support, that the exposed conductor surface is formed by a surface in a first end of the pin, and that the second end of the pin is connected to an insulated electrical cable, which cable exits the support and connects to the current signal module.

6. The irradiation device according to claim 3, wherein each conductor is a pin arranged through a hole in the support, that the exposed conductor surface is formed by a surface in a first end of the pin, and that the second end of the pin exits the support and forms a portion of a male part of a shielded pin connector, and wherein a female part of the shielded pin connector is adapted to be connected to the male part of the shielded pin connector and that a cable from the female part of the shielded pin connector is connected to the current signal module.

7. The irradiation device according to claim 2, wherein
    the dose processing module is in communication with an emitter control module and an irradiation control module,
    the second dose control parameters are adapted to be sent to the dose processing module from the emitter control module and the irradiation control module,
    the emitter control module is connected to means for measuring the current over a filament of the electron beam emitter and the voltage between the electron exit window and the filament, and
    the dose processing module is adapted to provide a feedback signal to the irradiation control module if the dose rate in one or several of the area units is not within an acceptable, pre-set dose rate range.

8. The irradiation device according to claim 1, wherein
    the conductors of the sensor device are arranged along a line being directed substantially perpendicular to a direction of the movement of the electron beam emitter over the sensor device, and
    the sensor device comprises a support in which the conductors are arranged, and wherein the conductors are electrically insulated from the support.

9. The irradiation device according to claim 8, wherein the sensing area of the sensor device at least covers the extension of the entire electron beam in a plane of the sensing area and wherein the first control parameter is detected once during the passage of the electron beam over the sensor device.

10. The irradiation device according to claim 1, wherein
    a first set of exposed conductor surfaces are arranged in a common first plane, the first plane being a first sensor surface and is aligned with a first portion of the sensing area, and
    the electron beam emitter and the sensor device are arranged such, in relation to each other, that when the electron beam emitter passes over the sensor device a plane, corresponding to the surface of the electron exit window, is moved in a direction parallel to the first plane of the sensor device.

11. The irradiation device according to claim 10, wherein a second set of exposed conductor surfaces are arranged in a common second plane, the second plane being a second sensor surface,
    being parallel to the first plane and spaced from the first plane in a direction substantially perpendicular to the plane of the electron exit window and away from the plane of the electron exit window, and
    being aligned with a second portion of the sensing area, and
    wherein the exposed conductor surfaces of the second set are arranged one after the other along a line, the line being aligned with the first direction.

12. The irradiation device according to claim 1, wherein
    the sensing area has a length in a first direction being larger than a longest extension of an area, along the first direction, passed by the electron beam, when the electron exit window is moved past the sensing area in a second direction being either perpendicular to the first direction or angled in relation to the first direction, the exposed conductor surfaces of the first set are arranged one after the other along a line, and the line is aligned with the first direction.

13. The irradiation device according to claim 1, wherein it is provided in a filling machine for use in sterilization of packaging containers, and comprises a first position being a packaging container infeed point, and a second position being a packaging container outfeed point, wherein, the electron beam emitter is adapted to perform a first movement from the first position to the second position, and during the first movement the electron beam emitter is adapted to be at least temporarily engaged with a packaging container for irradiating the packaging container, and the electron beam emitter is adapted to perform a second movement from the second position to the first position, and during the second movement the electron beam emitter is adapted to move past the sensor device such that the electron beam emitted from the electron exit window is adapted to be at least temporarily located within a sensing area of the sensor device.

14. Method for irradiating objects with an electron beam, the method comprising:

moving at least one electron beam emitter, which emits an electron beam through an electron exit window of the at least one electron beam emitter, past at least one sensor device, which detects a first dose control parameter of the electron beam, the sensor device comprising more than one conductor each having a conductor surface in a sensing area of the sensor device;

the at least one electron beam emitter being moved past the at least one sensor device such that the electron beam emitted from the electron exit window passes within the sensing area of the at least one sensor device; and exposing, to the electron beam, the conductor surface of each of the more than one conductor of the at least one sensor device.

15. The method according to claim 14, wherein the first dose control parameter is electrical current generated in the conductor, and including a dose processing module in communication with a current signal module, the method comprising:

measuring the electrical current using the current signal module; and collecting, by the dose processing module, first dose control parameter measurements made at different times, during the passage of the electron beam over the at least one sensor device, to generate an image of the electron beam.

* * * * *